United States Patent
Komorowski

(10) Patent No.: US 8,933,022 B2
(45) Date of Patent: Jan. 13, 2015

(54) METHODS AND COMPOSITIONS FOR THE TREATMENT AND PREVENTION HYPOGLYCEMIA AND RELATED DISORDERS

(75) Inventor: James R. Komorowski, Trumbull, CT (US)

(73) Assignee: JDS Therapeutics, LLC, Purchase, NY (US)

( * ) Notice: Subject to any disclaimer, the term of this patent is extended or adjusted under 35 U.S.C. 154(b) by 0 days.

(21) Appl. No.: 13/409,960

(22) Filed: Mar. 1, 2012

(65) Prior Publication Data

US 2012/0225134 A1  Sep. 6, 2012

Related U.S. Application Data

(60) Provisional application No. 61/448,134, filed on Mar. 1, 2011.

(51) Int. Cl.
| | |
|---|---|
| *A61K 38/28* | (2006.01) |
| *A61K 33/24* | (2006.01) |
| *A61K 31/28* | (2006.01) |
| *A61P 3/10* | (2006.01) |
| *A61P 25/00* | (2006.01) |
| *A61P 25/08* | (2006.01) |
| *A61P 25/16* | (2006.01) |
| *A61P 25/28* | (2006.01) |
| *A61P 3/04* | (2006.01) |
| *A61P 25/14* | (2006.01) |
| *A61P 5/50* | (2006.01) |
| *A61P 9/00* | (2006.01) |

(52) U.S. Cl.
CPC .................. *A61K 33/24* (2013.01); *A61K 38/28* (2013.01)
USPC .............................. 514/5.9; 530/304; 424/655

(58) Field of Classification Search
CPC .... A61K 33/24; A61K 38/28; A61K 2300/00
USPC .............................. 424/655; 514/5.9; 530/304
See application file for complete search history.

(56) References Cited

U.S. PATENT DOCUMENTS

| | | |
|---|---|---|
| 4,164,573 A | 8/1979 | Galinsky |
| 4,315,927 A | 2/1982 | Evans |
| 4,421,685 A | 12/1983 | Chance et al. |
| 4,424,057 A | 1/1984 | House |
| 4,476,118 A | 10/1984 | Brange et al. |
| 4,571,391 A | 2/1986 | Riley et al. |
| 4,954,492 A | 9/1990 | Jensen |
| 5,023,252 A | 6/1991 | Hseih |
| 5,053,389 A | 10/1991 | Balschmidt et al. |
| 5,057,320 A | 10/1991 | Evans et al. |
| 5,085,996 A | 2/1992 | Evans |
| 5,087,623 A | 2/1992 | Boynton |
| 5,087,624 A | 2/1992 | Boynton |
| RE33,988 E | 7/1992 | Evans |
| 5,164,384 A | 11/1992 | Paul |
| 5,175,156 A | 12/1992 | Boynton et al. |
| 5,194,615 A | 3/1993 | Jensen |
| 5,336,672 A | 8/1994 | Southern, Jr. et al. |
| 5,474,978 A | 12/1995 | Bakaysa et al. |
| 5,496,827 A | 3/1996 | Patrick |
| 5,534,488 A | 7/1996 | Hoffmann |
| 5,582,839 A | 12/1996 | McCarty |
| 5,597,585 A | 1/1997 | Williams et al. |
| 5,635,535 A | 6/1997 | Wagstaff |
| 5,643,957 A | 7/1997 | Leone-Bay et al. |
| 5,650,386 A | 7/1997 | Leone-Bay et al. |
| 5,707,970 A | 1/1998 | McCarty et al. |
| 5,721,114 A | 2/1998 | Abrahamsen et al. |
| 5,731,303 A | 3/1998 | Hsieh |
| 5,766,633 A | 6/1998 | Milstein et al. |
| 5,773,647 A | 6/1998 | Leone-Bay et al. |
| 5,776,498 A | 7/1998 | McCarty |
| 5,776,504 A | 7/1998 | McCarty |
| 5,776,888 A | 7/1998 | Leone-Bay et al. |
| 5,789,401 A | 8/1998 | McCarty |
| 5,804,688 A | 9/1998 | Leone-Bay et al. |
| 5,858,968 A | 1/1999 | Weiner et al. |
| 5,863,944 A | 1/1999 | Leone-Bay et al. |
| 5,866,536 A | 2/1999 | Leone-Bay et al. |
| 5,876,710 A | 3/1999 | Leone-Bay et al. |

(Continued)

FOREIGN PATENT DOCUMENTS

| | | | | |
|---|---|---|---|---|
| DK | 135268 | 2/1974 | | |
| EP | 0016496 | 10/1980 | | |
| EP | 0881649 | 12/1998 | | |
| IN | 2004MU01120 A | * 1/2007 | ................... | 424/655 |
| WO | WO 91/11117 | 8/1991 | | |
| WO | WO 95/28838 | 11/1995 | | |
| WO | WO 96/35421 | 11/1996 | | |
| WO | WO 98/25589 | 6/1998 | | |
| WO | WO 99/07387 | 2/1999 | | |
| WO | WO 00/06534 | 2/2000 | | |

(Continued)

OTHER PUBLICATIONS

Richard Anderson, Stability and Absorption of Chromium and Absorption of Chromium Histidinate Complexes by Humans, 2004, Biological Trace Element Research, vol. 101:211-217.*

(Continued)

*Primary Examiner* — Julie Ha
*Assistant Examiner* — Erinne Dabkowski
(74) *Attorney, Agent, or Firm* — Knobbe, Martens, Olson & Bear LLP

(57) ABSTRACT

A composition comprising chromium and insulin and/or a chromium-insulin complex, its method of preparation, and its use in the prevention and treatment of hypoglycemia and hypoglycemia-related conditions. This composition can be administered in numerous ways, including parenterally, intranasally, and orally. The composition stabilizes serum glucose levels and has a synergistic effect compared to chromium and insulin administered separately.

12 Claims, 17 Drawing Sheets

(56) References Cited

U.S. PATENT DOCUMENTS

| | | | |
|---|---|---|---|
| 5,876,757 A | 3/1999 | McCarty |
| 5,879,681 A | 3/1999 | Leone-Bay et al. |
| 5,914,326 A | 6/1999 | McCarty et al. |
| 5,929,066 A | 7/1999 | McCarty |
| 5,939,381 A | 8/1999 | Leone-Bay et al. |
| 5,955,503 A | 9/1999 | Leone-Bay et al. |
| 5,965,121 A | 10/1999 | Leone-Bay et al. |
| 5,989,539 A | 11/1999 | Leone-Bay et al. |
| 5,990,166 A | 11/1999 | Leone-Bay et al. |
| 6,001,347 A | 12/1999 | Leone-Bay et al. |
| 6,004,925 A | 12/1999 | Dasseux et al. |
| 6,037,323 A | 3/2000 | Dasseux et al. |
| 6,048,846 A | 4/2000 | Cochran |
| 6,051,561 A | 4/2000 | Leone-Bay et al. |
| 6,060,513 A | 5/2000 | Leone-Bay et al. |
| 6,071,510 A | 6/2000 | Leone-Bay et al. |
| 6,090,958 A | 7/2000 | Leone-Bay et al. |
| 6,099,869 A | 8/2000 | McCarty |
| 6,100,298 A | 8/2000 | Leone-Bay et al. |
| 6,140,304 A | 10/2000 | Sears |
| 6,156,735 A | 12/2000 | McCarty et al. |
| 6,203,823 B1 | 3/2001 | McCarty |
| 6,251,889 B1 | 6/2001 | de la Harpe et al. |
| 6,329,361 B1 | 12/2001 | McCarty |
| 6,344,444 B1 | 2/2002 | McCarty et al. |
| 6,358,504 B1 | 3/2002 | Leone-Bay et al. |
| 6,376,549 B1 * | 4/2002 | Fine et al. ............... 514/635 |
| 6,689,383 B1 | 2/2004 | Anderson et al. |
| 6,809,115 B2 | 10/2004 | Katz et al. |
| 7,112,561 B2 | 9/2006 | Gyurik et al. |
| RE39,480 E | 1/2007 | McCarty |
| 7,291,591 B2 | 11/2007 | Fishman |
| 7,429,564 B2 | 9/2008 | Arbit et al. |
| 8,062,677 B2 | 11/2011 | Komorowski |
| 2002/0081315 A1 | 6/2002 | Katz et al. |
| 2002/0098247 A1 | 7/2002 | Komorowski et al. |
| 2002/0197331 A1 | 12/2002 | Komorowski et al. |
| 2003/0091654 A1 | 5/2003 | Katz et al. |
| 2003/0211172 A1 | 11/2003 | Jones et al. |
| 2004/0005368 A1 | 1/2004 | Mann et al. |
| 2005/0069593 A1 | 3/2005 | Zwiefel |
| 2005/0214384 A1 | 9/2005 | Juturu et al. |
| 2005/0214385 A1 | 9/2005 | Komorowski et al. |
| 2005/0233946 A1 | 10/2005 | Fine et al. |
| 2006/0024383 A1 | 2/2006 | Berlin |
| 2007/0092584 A1 * | 4/2007 | Fine et al. ............... 424/646 |
| 2009/0155384 A1 | 6/2009 | Komorowski |
| 2010/0009015 A1 | 1/2010 | Juturu et al. |
| 2010/0262434 A1 | 10/2010 | Shaya |
| 2012/0100228 A1 | 4/2012 | Komorowski |
| 2012/0128794 A1 | 5/2012 | Komorowski |
| 2012/0225134 A1 | 9/2012 | Komorowski |

FOREIGN PATENT DOCUMENTS

| | | |
|---|---|---|
| WO | WO 00/07979 | 2/2000 |
| WO | WO 00/12095 | 3/2000 |
| WO | WO 00/15211 | 3/2000 |
| WO | WO 00/47188 | 8/2000 |
| WO | WO 00/50386 | 8/2000 |
| WO | WO 00/59863 | 10/2000 |
| WO | WO 01/21073 | 3/2001 |
| WO | WO 01/25679 | 4/2001 |
| WO | WO 01/25704 | 4/2001 |
| WO | WO 01/32130 | 5/2001 |
| WO | WO 01/32596 | 5/2001 |
| WO | WO 01/34114 | 5/2001 |
| WO | WO 01/41985 | 6/2001 |
| WO | WO 01/44199 | 6/2001 |
| WO | WO 01/51454 | 7/2001 |
| WO | WO 02/02509 | 1/2002 |
| WO | WO 02/04024 | 1/2002 |
| WO | WO 02/11564 | 2/2002 |
| WO | WO 02/19969 | 3/2002 |
| WO | WO 02/20466 | 3/2002 |
| WO | WO 02/24180 | 3/2002 |
| WO | WO 02/36127 | 5/2002 |
| WO | WO 02/36202 | 5/2002 |
| WO | WO 02/067953 | 9/2002 |
| WO | WO 02/069937 | 9/2002 |
| WO | WO 02/070438 | 9/2002 |
| WO | WO 03/043569 | 5/2003 |
| WO | WO 03/090671 | 11/2003 |
| WO | WO 2004/107881 | 12/2004 |
| WO | WO 2009/002867 | 12/2008 |
| WO | WO 2011/002939 | 1/2011 |
| WO | WO 2008/094939 | 5/2011 |
| WO | WO 2012/119007 | 9/2012 |

OTHER PUBLICATIONS

William J. Campbell, Interaction of insulin and chromium (III) on mitochondrial swelling, 1963, American Journal of Physiology, vol. 204:1028-1030.*

Samir Melki, Expression of the adipocyte fatty acid-binding protein in streptozotocin-diabetes: effects of insulin deficiency and supplementation, 1993, Journal of Lipid Research, vol. 34:1527-1534.*

Julie Martin, Chromium Picolinate Supplementation Attenuates Body Weight Gain and Increases Insulin Sensitivity in Subjects With Type 2 Diabetes, 2006, Diabetes Care, vol. 29:1826-1832.*

R. Sreekanth, Molecular Basis of Chromium Insulin Interactions, Biochemical and Biophysical Research Communications, 369, 2008, pp. 725-729.*

Anderson, "Chromium Metabolism and Its Role in Disease Processes in Man", Clin. Psychol. Biochem. 4:31-41 (1986).

Anderson, RA., "Nutritional factors influencing the glucose/insulin system: chromium", J Am Coll Nutr 16: 404-410, (1997).

Anderson et al., Metabolism 36(4):351-355 (1987).

Anderson et al., "Lack of Toxicity of Chromium Chloride and Picolinate", 16 J. Am. Coll. Nutr. 273-279 (1997).

Anderson, et al., "Stability and Absorption of Chromium and Absorption of Chromium Histidinate Complexes by Humans", Biological Trace Element Research, vol. 101; 211-218 (2004).

Anonymous: "Chrom bei Diabetes mellitus", (Oct. 31, 2010), Retrieved from the Internet: URL:http://web.archive.org/web/28181831894 712/http://www.diabetiker-experte.de/Chrom -bei-Diabetes-mellitus.html (retrieved on Apr. 20, 2012).

Aragno et al., Endocrinology 143(9):3250-3258 (2002).

Badimon et al., "Role of high density lipoproteins in the regression of atherosclerosis", Circulation 86: (Suppl. III) 86-94 (1992).

Bailey, M .M. et al., "Exposure of pregnant mice to chromium picolinate results in skeletal defects in their offspring", Birth Defects Research Part B: Developmental and Reproductive Toxicology, 77: 244-249 (2006).

Berge et al., "Pharmaceutical Salts", Journal of Pharmaceutical Sciences, pp. 1-19, vol. 66, No. 1 (1977).

Boyle et al., Southern Med. J. 70:1449-1453 (1977).

Castro et al., "Cardiometabolic Syndrome: Pathophysiology and Treatment", Curr Hypertens Rep. 5(5):393-401 (2003).

Cefalu, William T. et al., "The Effect of Chromium Supplementation on Carbohydrate Metabolism and Body Fat Distribution" Diabetes, p. 55A, vol. 46 (1997).

Christman et al., Brain Pathology 10:153-162 (2000).

Dansky and Fisher, "High-Density Lipoprotein and Plaque Regression: The Good Cholesterol Gets Even Better", Circulation 100:1762-3 (1999).

Davis et al., "Effects of Over-the-Counter Drugs on Chromium Retention and Urinary Excretion in Rats", J. Nutrition Res. 15:202-210 (1995 ).

Diem, et al., "Scientific Tables" Documenta Geigy, Seventh Edition, pp. 457-497 (1975).

Diplock, "Antioxidant Nutrients and Disease Prevention: An Overview" Am. J. Clin. Nutr., pp. 189-193, vol. 53 (1991).

Dorflinger, L.J., "Metabolic Effects of Implantable Steroid Contraceptives for Women", Contraception 65:47-62 (2002).

Drake et al. "Chromium Infusion in hospitalized patients with severe insulin resistance: a retrospective analysis." Endocr Pract. Jan. 31, 2012:1-17 [Epub ahead of print].

(56) References Cited

OTHER PUBLICATIONS

Evans, et al., "Chromium Picolinate Increases Membrane Fluidity and Rate of Insulin Internalization" Journal of Inorganic Biochemistry, 46:243-250 (1992).
Feng et al., Diabetes. A469 (2002 Annual Conference).
Fielding and Fielding, "Molecular Physiology of Reverse Cholesterol Transport", J Lipid Res. 36:211-228 (1995).
Gress et al., "Hypertension and Antihypertensive Therapy as Risk Factors for Type 2 Diabetes Mellitus", N. Eng. J. Med. 342:905-912 (2000).
Hayden and Ma, "Molecular Genetics of Human Lipoprotein Lipase Deficiency", Mol. Cell Biochem. 113:171-176 (1992).
Hou et al., Chin Med J (Engl). 120(19):1704-1709 (2007).
Jula et al., "Effects of Diet and Simvastatin on Serum Lipids, Insulin, and Antioxidants in Hypercholesterolemic Men", JAMA 287:598-605, 604 (2002).
Julius et al., "Antihypertensive Treatment of Patients with Diabetes and Hypertension", Am. J. Hypertens. 14:310S-316S, 313S (2001).
Juturu, et al., "Absorption and excretion of chromium from orally administered chromium chloride, chromium acetate and chromium oxide in rats" Trace Elements and Electrolytes, 20(1):23-28, (2003).
Juturu, "Cardiometabolic Syndrome—New Therapeutic Challenges", DPG Medical Nutrition Matters 26(2):1, 3-10 (2006).
Kamath et al., J. Nutrition 127:478-482 (1997).
Lastra et al., "Cardiometabolic Syndrome and Chronic Kidney Disease", Curr Diab Rep. 6(3):207-12 (2006).
Lindemann, et al., "Effect of chromium source on tissue concentration of chromium in pigs" J Anim Sci, 86: 2971-2978 (2008).
McCarty, Mark F. "The Case for Supplemental Chromium and a Survey of Clinical Studies With Chromium Picolinate", Journal of Applied Nutrition, 43(1):58-66 (1991).
Miranda, et al., "Effect of Chromium and Zinc on Insulin Signaling in Skeletal Muscle Cells" Biological Trace Element Research, 101:19-36, vol. 101 (2004).
Martin, et al., Diabetes Care. Aug. 2006; 29(8):1826-32.
Monster et al., "Oral Contraceptive Use and Hormone Replacement Therapy are Associated with Microalbuminuria", Arch Intern Med. 161:2000-2005 (2001).
Morrison et al., J. Neurochem. 114:1581-1589 (2010).
National Academy of Sciences, "Recommended Dietary Allowances", pp. 159-161 (1980).
Peterson, K.R., "Pharmacodynamic Effects of Oral Contraceptive Steroids on Biochemical Markers for Arterial Thrombosis", Danish Medical Bulletin, 49:43-60 (2002).
Pi-Sunyer, et al., "Chromium" Chapter 40, Present Knowledge in Nutrition, 5th Edition, pp. 571-577 (1984).
Preuss, et al., "Comparing metabolic effects of six different commercial trivalent chromium compounds" Journal of Inorganic Biochemistry, 102:1986-1990 (2008).
Ravina, A. et al.,"Clinical Use of the Trace Element Chromium (III) in the Treatment of Diabetes Mellitus" The Journal of Trace Elements in Experimental Medicine, 8:183-190 (1995).
Reed et al., "A New Rat Model of Type 2 Diabetes: The Fat-fed, Streptozotocin-treated Rat" Metabolism 49(11):1390-1394 (2000).
Robins and Fasulo, "High Density Lipoproteins, But Not Other Lipoproteins, Provide a Vehicle for Sterol Transport to Bile", J. Clin. Invest. 99:380-384 (1997).
Schwartz, "Present Knowledge in Nutrition," p. 571, fifth edition (1984, the Nutrition Foundation, Washington, DC.
Sekine et al., Am. J Physiol Renal Physiol 290:F251-F261 (2006).
Spady, D.K., Reverse Cholesterol Transport and Atherosclerosis Regression, 100:576-578 (1999).
Sreekanth, R. et al., "Molecular basis of chromium insulin interactions", Biochemical and Biophysical Research Communications, 369: 725-729 (2008).
Thomas et al., JPET 311:456-466 (2004).
Wang et al., "Homozygous Disruption of Pctp Modulates Atherosclerosis in Apolipoprotein E-Deficient Mice", J Lipid Res. 47:2400-07 (2006).
Wang et al., "Involvement of Organic Cation Transporter 1 in Hepatic and Intestinal Distribution of Metformin", Journal of Pharmacology and Experimental Therapeutics, vol. 302, No. 2, pp. 510-515, 2002.
Web site of the American Heart Association (http://www.americanheart.org/cholesterol/about_level.html).
Web site of the National Cholesterol Education Program of the National Heart, Lung and Blood Institute (http://www.nhlbi.nih.gov/health/public/heart/chol/hbc_what.htm), and associated publication "High Blood Cholesterol—What You Need to Know."
Zhang, et al., "Dynamic expression of glucose transporters 1 and 3 in the brain of diabetic rats with cerebral ischemia reperfusion", Chin Med J 2009, 122 (17); 1996-2001.
International Search Report/Written Opinion for International Application No. PCT/US2012/027342, dated May 3, 2012.
Alberti, et al: "Definition, Diagnosis and Classification of Diabetes Mellitus and it's Complications Part 1: Diagnosis and Classification of Diabetes Mellitus Provisional Report of a WHO Consultation", *Diabet Med* 15: 539 (1998).
Uehara et al. "Chronic insulin hypoglycemia induces GLUT-3 protein in rat brain neurons", (1997) *Am. J. Physiol.* 272:E716-E719.
Reagan et al. "Regulation of GLUT-3 glucose transporter in the hippocampus of diabetic rats subjected to stress", (1999) *Am. J. Physiol. Endocrinol. Metab.* 276:E879-E886.
Katsumata et al. "Suboptimal energy balance selectively up-regulates muscle GLUT gene expression but reduces insulin-dependent glucose uptake during postnatal development", (1999)*FASEB J.*11:1405-13.
Kalaria et al. "Reduced Glucose Transporter at the Blood-Brain Barrier and in Cerebral Cortex in Alzheimer Disease", (1989) *J. Neurochem.* 53:1083-1088.
Simpson et al. "Decreased Concentrations of GLUT1 and GLUT3 Glucose Transporters in the Brains of Patienets with Alzheimer's Disease", (1994) *Ann. Neurol.* 35:546-551.
Petersen, et al.: "Mild Congnitive Impairment", *Arch Neurol* (1999) 56:303-308.
Gamberino et al. "Glucose Transporter Isoform Expression in Huntington's Disease Brain", (1994) *J. Neurochem.* 63:1392-1397.
Mazziotta, et al. "Reduced Cerebral Glucose Metabolism in Asymptomatic Subjects At Risk for Huntington's Disease", (1987) *New England J. Med.* 316:357-362.
Cornford, et al. "Dynamic [$^{18}$F ]Fluorodeoxyglucose Positron Emission Tomography and Hypometabolic Zones in Seizures: Reduced Capillary Influx", (1998) *Ann. Neurol.* 43:801-808.
Cornford et al. "High Expression of the Glut1 Glucose Transporter in Human Brain Hemangioblastoma Endothelium", (1998) *J. Neuropathol. Exp. Neurol.* 54:842-851.
Hannonen et al. "Neurocognitive functioning in children with type-1 diabetes with and without episodes of severe hypoglycaemia", (2003) *Developmental Medicine & Child Neurology* 45:4:262-268.
Rangasamy et al. "Genetic ablation of Nrf2 enhances susceptibility to cigarette smoke-induced emphysema in mice", (2004) *J Clin Invest* 114:1248.
Wallin et al. "Glial Fibrillary Acidic Protein in the Cerebrospinal Fluid of Patients with Dementia", (1996) *Dementia* 7:267.
Brun et al. "Synapse Loss and Gliosis in the Molecular Layer of the Cerebral Cortex in Alzheimer's Disease and in Frontal Lobe Degeneration", (1995) *Neurodegeneration* 4:171.
Markesbery et al. "Oxidative Alterations in Alzheimer's Disease", (1999) *Brain Pathol* 9(1):133-46.
Sayre et al. "4-Hydroxynonenal-Derived Advanced Lipid Peroxidation End Products are Increased in Alzheimer's Disease", (1997) *J Neurochem* 68(5):2092-2097.
Yoritaka et al. "Immunohistochemical detection of 4-hydroxynonenal protein adducts in Parkinson disease", (1996) *Proc. Natl. Acad. Sci. USA* 93:2696-2701.
Szatmari "The Epidemioligy of Attention-Deficit Hyperactivity Disorders", (1982) *Child Adolesc. Psychiat. Clin. North Am.* 1:361-371.
Ravina et al. "Clinical Use of the Trace Element Chromium (III) in the Treatment of Diabetes Mellitus", (1995) *J. Trace Elements in Experimental Med.* 12:71-83.

(56) References Cited

OTHER PUBLICATIONS

Recommended Daily Allowances, Ninth Revised Edition, The National Academy of Sciences, p. 160, 1980.

Govindaraju et al., "Chromium(III)—Insulin Derivatives and Their Implication in Glucose Metabolism", Journal of Inorganic Biochemistry, 35:137-147 (1989).

Govindaraju et al., "Chymotrypsin-Catalyzed Hydrolysis of Chromium(III) Derivatives of Insulin: Evidence for Stabilization of the Protein Through Interactions with Metal Ions", Journal of Inorganic Biochemistry, 35:127-135 (1989).

International Search Report dated May 3, 2012 for International Application No. PCT/US2012/027342.

* cited by examiner

Effect of insulin-chelate type on glucose level of type-1 diabetes induced rats (n=7 per group). Group, time, and group by time interaction effects were significant ($p < 0.0001$ for all).

Mean ± SEM (N=5/group). * P<0.05, ** P<0.01, Znc-In vs regular insulin (R-In).

Mean ± SEM (N=5/group). * P<0.05, and ** P<0.01, Cr-In or Znc-In vs regular insulin (R-In).

METHODS AND COMPOSITIONS FOR THE TREATMENT AND PREVENTION HYPOGLYCEMIA AND RELATED DISORDERS

CROSS-REFERENCE TO RELATED APPLICATIONS

This application claims priority to U.S. Provisional Patent Application No. 61/448,134, entitled "METHODS AND COMPOSITIONS FOR THE TREATMENT AND PREVENTION OF HYPOGLYCEMIA AND RELATED DISORDERS," filed Mar. 1, 2011, the entire content of which is hereby incorporated by reference.

BACKGROUND OF THE INVENTION

1. Field of the Invention

The embodiments disclosed herein relate to compositions for the treatment and prevention of hypoglycemia and hypoglycemia-related conditions, e.g., arising from insulin administration, and methods of making and using the same. Also provided are improved methods of administering insulin and treating diabetes.

2. Background of the Invention

Glucose-Metabolism Related Diseases and Disorders

Many diseases and disorders have been associated—etiologically or otherwise—to impaired, altered, or abnormal glucose metabolism. These diseases and disorders include, but are not limited to: diabetes (hyperglycemia); hypoglycemia; cardiometabolic syndrome; Alzheimer's disease; Huntington's disease; epilepsy; ischemia; Parkinson's disease; amnesia; dementia; mild cognitive impairment (MCI); attention deficit hyperactivity disorder (ADHD); amyotrophic lateral sclerosis (ALS); and, traumatic brain injury.

Hypoglycemia

Hypoglycemia is a term that literally means "low blood sugar." Hypoglycemia includes a state of a blood glucose level of not higher than about 60 mg/dL, but is not limited to this blood glucose level. For example, when a person having high blood glucose due to diabetes or the like undergoes a reduction in blood glucose level upon insulin injection or the administration of an antidiabetic agent, or when a healthy individual undergoes rapid reduction in blood glucose level due to hunger or strenuous exercise, similar conditions to hypoglycemia can appear even at about 100 mg/dL. Hypoglycemia often arises as a side effect of diabetes treatment (e.g., administration of insulin). Hypoglycemia can also result, however, from other medications or diseases, hormone or enzyme deficiencies, or tumors. Furthermore, hypoglycemia can result from a long-term habit of ingesting large amounts of carbohydrates; from excessive ingestion of alcohol; and from continuation of extreme exercise for a long time in a state of dietary insufficiency. Hypoglycemia induced by diabetes treatment or other medications are particularly dangerous, however, resulting in a higher probability of a severe condition as compared to other causes of hypoglycemia.

Hypoglycemia-related disorders and hypoglycemia-related complications refer to conditions or complications that arise as a result of low blood sugar, such as insulin-induced brain tissue damage, and the like. Hypoglycemia-related disorders and hypoglycemia-related conditions may occur where a reduction in glucose level in blood is accompanied by a reduction in glucose level in the brain thereby causing lassitude, general discomfort, dismay, malaise, jitteriness, trembling, headache, weakness, cold sweat and palpitation, additionally causing impaired consciousness and coma, which may also lead to death in a serious case.

Diabetes Mellitus

Diabetes mellitus is known to affect at least 10 million Americans, and millions more may unknowingly have the disease. Diabetes is the sixth leading cause of death in the United States and accounted for more than 193,000 deaths in 1997. Diabetes is a disease state in which the pancreas does not release insulin at levels capable of controlling glucose levels. Diabetes is classified into two types. The first type is diabetes (Type 1) that is insulin dependent and usually appears in young people. The islet cells of the pancreas stop producing insulin mainly due to autoimmune destruction. Standard therapy for Type 1 diabetes is the administration of insulin. Type 1 diabetic patients are the minority of total diabetic patients (up to 10% of the entire diabetic population). The second type of diabetes (Type 2) is non-insulin dependent diabetes, which is caused by a combination of insulin resistance and insufficient insulin secretion. This is the most common type of diabetes in the Western world. Close to 8% of the adult population of various countries around the world, including the United States, have Type 2 diabetes, and about 30% of these patients will need to use insulin at some point during their life span due to secondary pancreas exhaustion.

The American Diabetes Association (ADA), World Health Organization (WHO) and Japan Diabetes Society (JDS) recently announced new diagnostic criteria for diabetes, taking into consideration the achievements of clinical and epidemiologic studies. Under these criteria, one is classified as diabetic when any of the following blood glucose levels are observed: fasting blood glucose≥126 mg/dL; casual blood glucose≥200 mg/dL; or blood glucose two hours after the 75 g oral glucose tolerance test (OGTT)≥200 mg/dL (*Diabetes Care* 20: 1183 (1997); *Diabet Med* 15: 539 (1998); and *Diabetes* 42: 385 (1999)).

Type 1 diabetics and many Type 2 diabetics, must manage their blood glucose concentration with administration of insulin multiple times a day because their pancreas is not capable of producing adequate insulin which is necessary to support glucose metabolism. The goal of administrating the proper insulin dose is to maintain blood glucose concentrations close to the physiological norm, which is approximately 1 gram of glucose per liter of blood, or 100 mg/dL. If not enough insulin is administered, the blood glucose level can reach hyperglycemic levels, leading to adverse health complications. Conversely, if too much insulin is administered, glucose levels can fall significantly below normal, creating a serious acute condition called hypoglycemia. It is a problem for a diabetic patient to know his of her immediate requirement for insulin, and it is not uncommon for diabetic patients to be off a factor of 2 or 3 from the desirable euglycemic target of 100 mg/dL. Poorly managed, the subject's blood glucose can alternate from hyperglycemic to hypoglycemic, or vice versa, in less than an hour. Hypoglycemia, if left untreated, can lead to seizures, brain damage, coma, or death. Thus, there is a need for improved methods of managing blood glucose levels with insulin.

Brain Glucose Metabolism/Transporters and Associated Diseases and Disorders

Glucose homeostasis is critical for energy generation, neuronal maintenance, neurogenesis, neurotransmitter regulation, cell survival and synaptic plasticity. Glucose is the principle energy source for mammalian brain, and a key role in cognitive function.

Delivery of glucose from the blood to the brain requires its transport across the endothelial cells of the blood-brain barrier and across the plasma membranes of neurons and glia, which is mediated by the facilitative glucose transporter proteins. Facilitative glucose transport is mediated by one or more members of the closely-related glucose transporter (GLUT) family. Thirteen members of the GLUT family have been described thus far. Tissue-specific glucose transporters allocate glucose among organs in order to maintain brain glucose concentrations. The two primary glucose transporter isoforms which function in cerebral glucose metabolism are GLUT-1 and GLUT-3. GLUT-1 is the primary transporter in the blood-brain barrier, choroid plexus, ependyma, and glia; GLUT-3 is the neuronal glucose transporter. GLUT-4, on the other hand, carries glucose across the membranes of muscle and fat cells.

Insulin, a regulator of glucose uptake, is secreted by the pancreas. Insulin allocates glucose to muscle and fat. The hypothalamus-pituitary-adrenal (HPA) axis, the sympathetic nervous system (SNS), and vascular endothelial growth factor allocate glucose to the brain. Feedback pathways both from the brain and from muscle and fat are involved in regulating glucose allocation and exogenous glucose supply. Further, insulin can cross the blood-brain barrier (BBB), reaching neurons and glial cells, and can exert a region-specific effect on glucose metabolism. Increased glucose consumption causes an increase in the net transport of glucose from blood to brain. It has been shown that insulin-induced hypoglycemia increases brain GLUT-1 & GLUT-3 levels. (Uehara et al. (1997) *Am. J. Physiol.* 272:E716-E719). Thus, insulin indirectly affects the transport without acting on the transport mechanisms. It has been proposed that part of the insulin action may take place in extracerebral tissues via changes of the amino acid balance in the blood. (Reagan et al. (1999) *Am. J. Physiol. Endocrinol. Metab.* 276:E879-E886).

GLUT-1 facilitates transport of glucose across the blood-brain-barrier. GLUT-1 expression levels are insulin-independent. Rather, GLUT-1 is dependent on potent regulators of blood vessel function like vascular endothelial growth factor (VEGF), a pituitary counter regulatory hormone. HPA-axis overdrive causes metabolic abnormalities such as central adiposity, hyperglycemia, dyslipidemia, and hypertension, that are well known clinical aspects the metabolic syndrome. Overexpression of GLUT-1 in skeletal muscle is associated with marked increases in lactate and glycogen due to an increase in basal glucose uptake, and increased glucose flux results in resistance of GLUT-4 to activation by insulin and other stimuli, such as hypoxia and contractile activity (Katsumata et al. (1999) *FASEB J.* 11:1405-13).

GLUT-3, the neuron-specific glucose transporter, is solely responsible for the delivery of glucose into neurons in the central nervous system. GLUT-3 mRNA is widely expressed in the brain, including the pyramidal neurons of the hippocampus, the granule neurons of the dentate gyrus, and the cortex.

Brain-specific kinases 1 and 2 (BRSK1/2) are AMP-activated protein kinase (AMPK)-related kinases that are highly expressed in mammalian forebrain. The activation of AMPK plays an important, albeit not an exclusive, role in the induction of recruitment of the insulin-dependent glucose transporter found in skeletal muscle, GLUT-4, to the plasma membrane. The ability of AMPK to stimulate GLUT-4 translocation to the plasma membrane in skeletal muscle occurs via a mechanism distinct from that stimulated by insulin since together insulin and AMPK effects are additive. In addition to its role in the regulation of GLUT-4, data suggest that AMPK regulates glucose transport through GLUT-1.

Altered glucose metabolism in the brain is associated with various disease states, including but not limited to Alzheimer's disease, Huntington's disease, epilepsy, ischemia, amnesia, and traumatic brain injury. Glucose transporter expression is believed to be related to altered glucose metabolism. Chronic hyperglycemia downregulates GLUT-1 and GLUT-3 expression at both mRNA and protein levels in the brain, which is not due to the decrease of the density of microvessels. (Hou et al. (2007) *Chin Med J (Engl).* 120(19): 1704-1709). The downregulation of GLUT-1 and GLUT-3 expression might be the adaptive reaction of the body to prevent excessive glucose entering the cell that may lead to cell damage. Studies suggest that chronic stress produces molecular, morphological, and ultrastructural changes in the hippocampus that are accompanied by cognitive deficits. Further, in insulin resistance, dementia, and cognitive impairment, and Alzheimer's disease, there is a reduced sensitivity to insulin resulting in hyperinsulinemia. Toxic levels of insulin negatively influence neuronal function and survival, and elevation of peripheral insulin concentration acutely increases its cerebrospinal fluid (CSF) concentration. Peripheral hyperinsulinemia correlates with an abnormal removal of the amyloid beta peptide (Abeta) and an increase of tau hyperphosphorylation as a result of augmented cdk5 and GSK3beta activities. This leads to cellular cascades that trigger a neurodegenerative phenotype and decline in cognitive function.

In Alzheimer's disease, glucose metabolism is decreased and is associated with decreased amounts of GLUT-1 protein in cerebral microvessels in the frontal cortex and hippocampus, the regions most affected. (Kalaria et al. (1989) *J. Neurochem.* 53:1083-1088). Likewise, GLUT-3 levels have been reported to be reduced in the brains of patients with Alzheimer's Disease. (Simpson et al. (1994) *Ann. Neurol.* 35:546-551).

Studies have suggested that a condition termed mild cognitive impairment (MCI) represents prodromal Alzheimer's disease and if diagnosed early represents the best opportunity for pharmaceutical intervention. The clinical criteria used for diagnosis of MCI are those of Petersen et al. (*Arch Neurol* (1999) 56:303-308) and include: memory complaints corroborated by an informant; objective memory impairment for age and education; normal general cognitive function; intact activities of daily living; and, the subject does not meet criteria for dementia.

Huntington's disease is a neurodegenerative disorder. Early stages of the disease are characterized by subtle changes in personality, cognition, or physical skills. The most characteristic initial physical symptoms is chorea, characterized by jerky, random, and uncontrollable movements. Chorea is often initially exhibited as general restlessness, small unintentionally initiated or uncompleted motions, uncoordination, or slowed saccadic eye movements. Symptoms such as rigidity, repetitive motions or abnormal posturing appear as the disorder progresses. These symptoms are regarded as the onset stage of the disease, and gradually become the dominant physical symptoms. Juvenile Huntington's Disease differs from these symptoms, in that it generally progresses faster and chorea is exhibited briefly, if at all, with rigidity being the dominant symptom. Additionally, seizures are a common symptom of Juvenile Huntington's Disease. In Huntington's disease, GLUT-1 and GLUT-3 levels are decreased in the caudate portion of the brain. (Gamberino et al. (1994) *J. Neurochem.* 63:1392-1397). Decreases in caudate glucose metabolism have been reported in subjects with both symptomatic and clinically asymptomatic subjects at risk for Huntington's Disease. (Mazziotta, et al. (1987) *New England J. Med.* 316:357-362).

Glucose transport is also decreased in the human epileptic brain, due at least in part to decreased expression of GLUT-1 at the blood brain barrier endothelium (Cornford, et al. (1998) *Ann. Neurol.* 43:801-808; Cornford et al. (1998) *J. Neuropathol. Exp. Neurol.* 54:842-851).

Idiopathic epilepsy has a greater incidence amongst the Type 1 diabetic population than the greater population (Hannonen et al. (2003) *Developmental Medicine & Child Neurology* 45:4:262-268). Meanings inferred from the results could be interpreted in several ways. Diabetes could be partly responsible for idiopathic generalized epilepsy, or the two conditions could have different ages of onset. Metabolic abnormalities including hyperglycemia, mild hyperosmolality and hyponatremia contribute to the development of epilepsiapartialis continua in an area of focal brain damage. Occipital seizures and hemianopsia can be caused by hyperglycemia and may be accompanied by special MRI and VEP findings. The increased incidence of seizure and delayed neuronal damage resulting from pre-ischemic hyperglycemia corresponds with corticosterone levels rather than with glucose levels and suggests that corticosterone has a greater prognostic value than glucose in predicting cerebral ischemic damage.

GLUT-1 deficiency syndrome is a disorder that primarily affects the brain. Affected individuals generally have seizures beginning in the first few months of life. Infants with GLUT-1 deficiency syndrome have a normal head size at birth, but growth of the brain and skull is often slow, in severe cases resulting in an abnormally small head size (microcephaly). Subjects with GLUT-1 deficiency syndrome often exhibit developmental delay or intellectual disability. GLUT-1 deficiency syndrome is also associated with other neurological problems, such as stiffness caused by abnormal tensing of the muscles (spasticity), difficulty in coordinating movements (ataxia), and speech difficulties (dysarthria). Some experience episodes of confusion, lack of energy (lethargy), headaches, muscle twitches (myoclonus), or involuntary irregular eye movements, particularly before meals.

Other markers associated with brain glucose metabolism and transport-related diseases and disorders include Nrf2 (nuclear factor erythroid 2 related factor 2), GFAP (glial fibrillary acidic protein), and HNE (4-Hydroxynonenal).

Nrf2 (nuclear factor erythroid 2 related factor 2) is a regulator of multiple cytoprotective proteins. Nrf2 is a transcription factor that positively regulates a transcriptional program that maintains cellular redox homeostasis and protects cells from oxidative insult (Rangasamy et al. (2004) *J Clin Invest* 114:1248). Nrf2 activates transcription of its target genes through binding specifically to the antioxidant-response element (ARE) found in those gene promoters. Decreased levels of Nrf2 have been associated with high fat diets, and have been shown to lead to oxidative stress and cognitive impairment. (Morrison et al. (2010) *J. Neurochem.* 114:1581-1589).

GFAP (Glial fibrillary acidic protein) is a marker of neuronal damage. GFAP is an intermediate filament protein found almost exclusively in astrocytes which, in adults, control the level of GFAP expression. Astrocytes are a major type of glial cell which perform a variety of structural and metabolic functions, such as processing neurotransmitters, controlling extracellular ion levels, regulating the direction and amount of nerve growth, maintaining the blood-brain barrier, and participating in immune reactions. As astrocytes transform from a resting state into a process-bearing reactive state during events such as aging, GFAP expression is up-regulated. GFAP levels have been shown to increase in the brain tissue and cerebrospinal fluid in patients suffering from Alzheimer's disease, and it has been suggested that reactive astrocytes may contribute to the neuropathology of Alzheimer's disease (Wallin et al. (1996) *Dementia* 7:267). In the Alzheimer's diseased brain, the loss of synapses is associated with an increase in the number of GFAP-positive astrocytes. In addition, this loss of synapses appears to be related to the extent of reactive astrogliosis (Brun et al. (1995) *Neurodegeneration* 4:171). GFAP is a major component of the gliotic scars which result from gliosis, and which may interfere with subsequent reinnervation.

HNE (4-Hydroxynonenal) is a marker of oxidative stress, linked to Alzheimer's and Parkinson's disease. Increased levels of HNE have been detected in brains with Alzheimer's disease (Markesbery et al. (1999) *Brain Pathol* 9(1):133-46; Sayre et al. (1997) *J Neurochem* 68(5):2092-2097). HNE is an $\alpha,\beta$-unsaturated aldehyde that is produced during oxidation of membrane lipid polyunsaturated fatty acids. It is one of the major products of membrane peroxidation and is considered to be largely responsible for cytotoxic effects observed under the oxidative stress. HNE exhibits variable adverse effects such as inhibition of DNA, RNA, and protein synthesis, interference with certain enzyme activities, and induction of heat shock proteins (Yoritaka et al. (1996) *Proc. Natl. Acad. Sci. USA* 93:2696-2701).

Parkinson's disease is a progressive disorder that affects a small area of cells (called the substantia Nigra) in the middle part of the brain and which occurs slightly more often in men than women. It is also called Shaking palsy or paralysis agitans and is a disorder of the central nervous system primarily attacking people between the ages 50 and 69. Approximately one out of every 1,000 people contact the illness. One known cause of Parkinson's disease is the degeneration and death of cells which normally produce dopamine, a chemical necessity for transmitting messages in the brain. This causes a deficiency of dopamine and perhaps consequentially the symptoms of Parkinson's disease. The common symptoms include tremor, stiffness (or rigidity) of muscles, slowness of movement (bradykinesia) and loss of balance (postural dysfunction). Parkinson's disease is one of the most prevalent neurological conditions—along with epilepsy, stroke and dementia. The natural history of the disease results in a rate of progression from 10-15 years from onset of the disease, to disability, with some variability from patient to patient. Parkinson's itself, moreover, the disability caused by the disease often leads to fatal infections such as aspiration, pneumonia, and urinary tract infections.

Parkinson's disease is usually categorized into three distinct groups. Paralysis agitans usually called Parkinson's disease is the most common form of Parkinsonism, afflicting approximately 75% of the cases and is of unknown origin or cause. The second type of Parkinsonism which is caused by drugs and toxins, which include carbon monoxide, manganese and chemical compound called MPTP (methyl-phenyltetrahydropyridine). The third form of Parkinsonism is called Vascular Parkinsonism which may be caused by multiple small strokes which damage the dopamine-producing brain cells.

ADHD refers clinically to a relatively common syndrome (epidemiologic studies have suggested that the prevalence of ADHD among the general population is between 2-10%). ADHD begins in childhood and typically remits by adulthood (Szatmari (1982) *Child Adolesc. Psychiat. Clin. North Am.* 1:361-371). ADHD is clinically characterized by inattention (e.g. failure to give close attention, difficulties in sustaining attention, difficulties in organising tasks and activities and easily distracted by extraneous stimuli), hyperactivity (e.g. difficulties in remaining seated, excessive motor activity in inappropriate situations, the patient acts as if "driven by a motor"), and impulsivity (e.g. difficulties in awaiting turn, answer questions before they have been completed and often interrupts or intrudes ongoing conversation). (American Psychiatric Association, Diagnostic and Statistical Manual of Mental Disorders (DSM-IV), 1994).

Chromium

Chromium is a nutritionally essential trace element. The essentiality of chromium in the diet was established in 1959 by Schwartz. (Schwartz, "Present Knowledge in Nutrition," page 571, fifth edition (1984, the Nutrition Foundation, Washington, D.C.)). Chromium is essential for optimal insulin activity in all known insulin-dependent systems (Boyle et al. (1977) *Southern Med. J.* 70:1449-1453). Chromium depletion is characterized by the disturbance of glucose, lipid and protein metabolism and by a shortened lifespan. Insufficient dietary chromium has been linked to both maturity-onset diabetes and to cardiovascular disease.

Dietary supplementation of chromium to normal individuals has been reported to lead to improvements in glucose tolerance, serum lipid concentrations, including high-density lipoprotein cholesterol, insulin and insulin binding. (Anderson (1986) *Clin. Psychol. Biochem.* 4:31-41). Supplemental chromium in the trivalent form, e.g. chromic chloride, is associated with improvements of risk factors associated with adult-onset (Type 2) diabetes and cardiovascular disease. Chromium supplementation has been shown to reduce hyperglycemia, as well as promote weight loss, as described in U.S. Pat. Nos. 5,929,066, 6,329,361, and 6,809,115, which are each hereby incorporated by reference in their entirety. In a clinical study, Anderson et al. (*Metabolism* (1987) 36(4):351-355, 1987), chromium supplementation was shown to alleviate hypoglycemic symptoms and raise serum glucose levels out of the hypoglycemic range. In another study, chromium supplementation to overweight children with Type 1 diabetes did not result in any cases of hypoglycemia (May, 2007). In yet another study, chromium supplementation to adults with Type 1 diabetes did not result in any cases of hypoglycemia; and allowed a 50% reduction in insulin dose (Ravina et al. (1995) *J. Trace Elements in Experimental Med.* 12:71-83).

The principal energy sources for the body are glucose and fatty acids. Chromium depletion results in biologically ineffective insulin and compromised glucose metabolism. Under these conditions, the body relies primarily upon lipid metabolism to meet its energy requirements, resulting in the production of excessive amounts of acetyl-CoA and ketone bodies. Some of the acetyl-CoA can be diverted to increased cholesterol biosynthesis, resulting in hypercholesterolemia. Diabetes mellitus is characterized in large part by glycosuria, hypercholesterolemia, and often ketoacidosis. The accelerated atherosclerotic process seen in diabetics is associated with hypercholesterolemia. (Boyle et al. (1977) *Southern Med. J.* 70:1449-1453).

Chromium functions as a cofactor for insulin. It binds to the insulin receptor and potentiates many, and perhaps all, of its functions. (Boyle et al. (1977) *Southern Med. J.* 70:1449-1453). These functions include, but are not limited to, the regulation of carbohydrate and lipid metabolism. (Schwartz, "Present Knowledge in Nutrition," page 571, fifth edition (1984, the Nutrition Foundation, Washington, D.C.)). The introduction of inorganic chromium compounds per se into individuals is not particularly beneficial. Chromium must be converted endogenously into an organic complex or must be consumed as a biologically active molecule. Only about 0.5% of ingested inorganic chromium, however, is assimilated into the body. (Recommended Daily Allowances, Ninth Revised Edition, The National Academy of Sciences, page 160, 1980). Only 1-2% of most organic chromium compounds are assimilated into the body.

U.S. Pat. Nos. 4,315,927 and Re. 33,988 disclose that when selected essential metals, including chromium, are administered to mammals as exogenously synthesized coordination complexes of picolinic acid, they are directly available for absorption without competition from other metals. Describes therein are compositions and methods for selectively supplementing the essential metals in the human diet and for facilitating absorption of these metals by intestinal cells. These complexes are safe, inexpensive, biocompatible, and easy to produce. The exogenously synthesized essential metal coordination complexes of picolinic acid (pyridine-2-carboxylic acid) have the following structural formula:

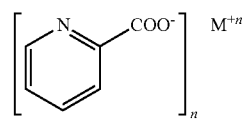

wherein M represents the metallic cation and n is equal to the cation's valence. For example, when M is Cr and n=3, then the compound is chromic tripicolinate. Other chromium picolinates disclosed include chromic monopicolinate and chromic dipicolinate.

The U.S. Recommended Daily Intake (RDI) of chromium is 120 μg. U.S. Pat. No. 5,087,623, the entire contents of which are hereby expressly incorporated herein by reference, describes the administration of chromic tripicolinate for the treatment of adult-onset diabetes in doses ranging from 50 to 500 μg. U.S. Pat. No. 6,329,361, the entire contents of which are hereby expressly incorporated herein by reference, discloses the use of high doses of chromic tripicolinate (providing 1,000-10,000 μg chromium/day) for reducing hyperglycemia and stabilizing the level of serum glucose in humans with Type 2 diabetes. U.S. Pat. Nos. 5,789,401 and 5,929,066, the entire contents of which are hereby expressly incorporated herein by reference, disclose a chromic tripicolinate-biotin composition and its use in lowering blood glucose levels in humans with Type 2 diabetes.

U.S. Pat. Nos. 5,087,623; 5,087,624; and 5,175,156, the entire contents of which are hereby expressly incorporated herein by reference, disclose the use of chromium tripicolinate for supplementing dietary chromium, reducing hyperglycemia and stabilizing serum glucose, increasing lean body mass and reducing body fat, and controlling serum lipid levels, including the lowering of undesirably high serum LDL-cholesterol levels and the raising of serum High Density Lipid (HDL)-cholesterol levels. U.S. Pat. Nos. 4,954,492 and 5,194,615, the entire contents of which are hereby expressly incorporated by reference, describe a related complex, chromic nicotinate, which is also used for supplementing dietary chromium and lowering serum lipid levels. Picolinic acid and nicotinic acid are position isomers having the following structures:

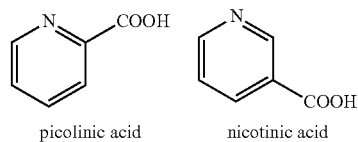 [SMILES: O=C(O)c1ccccn1 ; O=C(O)c1cccnc1]

picolinic acid  nicotinic acid

Nicotinic acid and picolinic acid form coordination complexes with monovalent, divalent and trivalent metal ions and facilitate the absorption of these metals by transporting them across intestinal cells and into the bloodstream. Chromium absorption in rats following oral administration of $CrCl_3$ was facilitated by the non-steroidal anti-inflammatory drugs (NSAIDs) aspirin and indomethacin. (Davis et al. (1995) *J. Nutrition Res.* 15:202-210; Kamath et al. (1997) *J. Nutrition* 127:478-482). These drugs inhibit the enzyme cyclooxygenase which converts arachidonic acid to various prostaglandins, resulting in inhibition of intestinal mucus formation and lowering of intestinal pH which facilitates chromium absorption.

There remains a constant need for effective treatments of hypoglycemia and hypoglycemia-related conditions. One such need is for safer and more optimal administrations of insulin. The present embodiments disclosed herein address this need by providing a safe, inexpensive, drug-free therapeutic agent, and methods of administering the same.

SUMMARY

The embodiments disclosed herein are based, in part, upon the surprising discovery of a novel chromium-insulin complex that has improved therapeutic efficacy and benefits. Thus, in accordance with the embodiments described herein, provided are compositions for the improved delivery of insulin and/or chromium, and uses thereof.

Some embodiments relate to compositions comprising a chromium-insulin complex. In some embodiments, the chromium-insulin complex comprise a stoichiometric ratio of chromium to insulin, e.g., 2:1, 1:1, 1:2, 1:3, 1:4, 1:5, 1:6, 1:7, 1:8, 1:9, 1:10. In some embodiments, the chromium and insulin are present in the chromium insulin complexes in non-stoichiometric amounts, e.g., between 1 and 10 molecules of chromium (e.g., chromium complex), per insulin molecule, or per insulin hexamer. In some embodiments the complex has a molecular weight that is between about 30 and 40 kDa, e.g., 30 kDa, 31 kDa, 32 kDa, 33 kDa, 34 kDa, 35 kDa, 36 kDa, 37 kDa, 38 kDa, 39 kDa, 40 kDa, or more.

The improved compositions comprising chromium-insulin complexes are useful for the delivery of insulin to individuals in need thereof, e.g., an individual that has a glucose metabolism disorder or condition, such as diabetes or hypoglycemia. In some embodiments, the compositions comprising a chromium-insulin complex exhibits improved absorption into the bloodstream, as compared to uncomplexed insulin, or other insulin complexes. In some embodiments, the compositions comprising a chromium-insulin complex exhibits more rapid decrease in serum glucose levels, when compared to uncomplexed insulin, or other insulin complexes. In some embodiments, the compositions comprising a chromium-insulin complex decreases weight loss associated with Type I diabetes. In some embodiments, the compositions comprising a chromium-insulin complex decreases weight gain associated with Type 2 diabetes.

Accordingly, some embodiments disclosed herein relate to compositions comprising chromium-insulin complexes. In some embodiments, the amounts of chromium and insulin in the composition are selected together to provide a therapeutically effective amount of chromium and or insulin. In some embodiments, a synergistically effective amount of chromium and insulin is provided to achieve greater than additive effect. In some embodiments, the chromium and insulin composition can be used to provide a greater therapeutic effect to a patient in need thereof than insulin alone, or compared to other insulin complexes, such as zinc-insulin.

In some aspects, the synergistically effective amount of chromium in the composition can be between about 5 and 2,000 micrograms. In some aspects, the synergistically effective amount of insulin is between about 1 unit and 500 units. In some aspects, the composition comprises a ratio of chromium to insulin between about 0.001 micrograms of chromium to units of insulin and 20 micrograms of chromium to units of insulin. In some aspects, the chromium is selected from the group of chromium complexes consisting of chromium picolinate, chromic tripicolinate, chromium nicotinate, chromic polynicotinate, chromium chloride, chromium histidinate, chromium trihistidinate, and chromium yeasts. Preferably, the chromium comprises a chromium histidinate. In some aspects, the composition provides increased insulin receptor binding. The chromium can be dissolved in a solution of the insulin or the chromium can be suspended in a solution of the insulin.

In accordance with the embodiments disclosed herein, provided is an improved method of administering insulin to a subject in need thereof, comprising combining insulin and chromium to create a composition, and administering the optimal dosage of the composition to the subject. The amounts of insulin and chromium can be synergistically effective amounts. The composition can comprise a chromium-insulin complex. In some embodiments, the subject has a glucose metabolism-related disease or disorder. In some aspects, the disease or disorder is selected from the group consisting of: diabetes, Alzheimer's disease, dementia, mild cognitive impairment (MCI), attention deficit hyperactive disorder (ADHD), Huntington's Disease, epilepsy, and Parkinson's Disease. In some embodiments, an optimal dosage of the composition comprising a chromium-insulin complex is determined for administration to the subject prior to administration of the composition to the subject.

In some embodiments, a method for making an injectable composition of chromium and insulin is provided that comprises combining chromium and insulin, thereby arriving at the injectable composition. The chromium can suspended in a solution of the chromium can be dissolved in a solution. The chromium and insulin injectable composition can comprise a chromium insulin complex. The injectable composition can be a suspension or a solution. In some aspects, the ratio of chromium to insulin is between 0.001 micrograms of chromium per unit of insulin and 100 micrograms of chromium per unit of insulin. In some embodiments, the composition is administered intranasally.

In some embodiments, a method for stabilizing serum glucose levels in an subject in need thereof is provided that comprises identifying a subject who is in need of insulin; and administering a composition comprising chromium and insulin to the subject. In some embodiments, the composition of chromium and insulin comprises a chromium-insulin complex. In some aspects, the composition of chromium and insulin is administered parenterally. In other aspects, the composition of chromium and insulin is administered orally. In some aspects, the composition of chromium and insulin is administered pulmonarily. In some aspects, the composition of chromium and insulin is administered nasally. In some embodiments, the subject has diabetes. In some embodiments, the subject is overweight. In some embodiments, the subject is identified as having diabetes-induced weight loss.

In some embodiments, use of a composition comprising chromium and insulin for stabilizing serum glucose levels in a subject in need thereof is provided. In some embodiments, the composition of chromium and insulin comprises a chromium-insulin complex. In some aspects, the composition of chromium and insulin is formulated for administration by injection. In other aspects, the composition of chromium and insulin is formulated for oral or intranasal administration. In some embodiments, the subject has diabetes. In some embodiments, the subject is overweight. In some embodiments, the subject is identified as having diabetes-induced weight loss.

Accordingly, in some embodiments, provided herein are methods to reduce the loss of weight associated with insulin administration, or stabilize the weight, in diabetic individuals receiving insulin therapy. Also provided are compositions comprising chromium and insulin for reducing loss of weight associated with insulin administration, stabilizing weight in diabetic individuals receiving insulin therapy. In some embodiments, the composition of chromium an insulin comprise an chromium-insulin complex. In some aspects the composition of chromium and insulin is formulated for administration by injection.

In some embodiments, an improved method for stabilizing serum glucose levels in a subject in need thereof is provided, wherein the improvement comprises administering insulin to the subject in the form of a composition comprising a chromium-insulin complex. In some embodiments, the composition comprises synergistically effective amounts of chromium and insulin. The composition can be administered parenterally, orally, pulmonarily, or transdermally. In some aspects, the synergistically effective amount of chromium is between about 300 and 1,000 micrograms. In some aspects, the synergistically effective amount of insulin is between about 5 units and 50 units. In some embodiments, the subject has a glucose metabolism-related disease or disorder.

In some embodiments, an improved method of treating diabetes, e.g., Type 1 or Type 2 diabetes, in a subject in need thereof with insulin comprises administering to the subject a composition comprising insulin and chromium. In some embodiments, the composition comprises a chromium-insulin complex. In some embodiments, the composition comprising insulin and chromium is administered parenterally. In some embodiments, the composition is administered nasally. In some embodiments, the composition is administered pulmonary. In some embodiments, the composition is administered transdermally. Some embodiments provide a composition comprising chromium and insulin for the treatment of diabetes, e.g., Type 1 or Type 2 diabetes. In some embodiments, the composition is formulated for administration by injection. In some embodiments, the composition comprises a chromium-insulin complex.

In some embodiments, method of preventing insulin-induced weight loss in a subject with diabetes comprises identifying a subject in need of insulin therapy for the treatment of diabetes administering to the subject a composition comprising insulin and chromium. In some aspects, the composition comprising insulin and chromium is administered parenterally.

DETAILED DESCRIPTION OF THE PREFERRED EMBODIMENT

Figure 1:
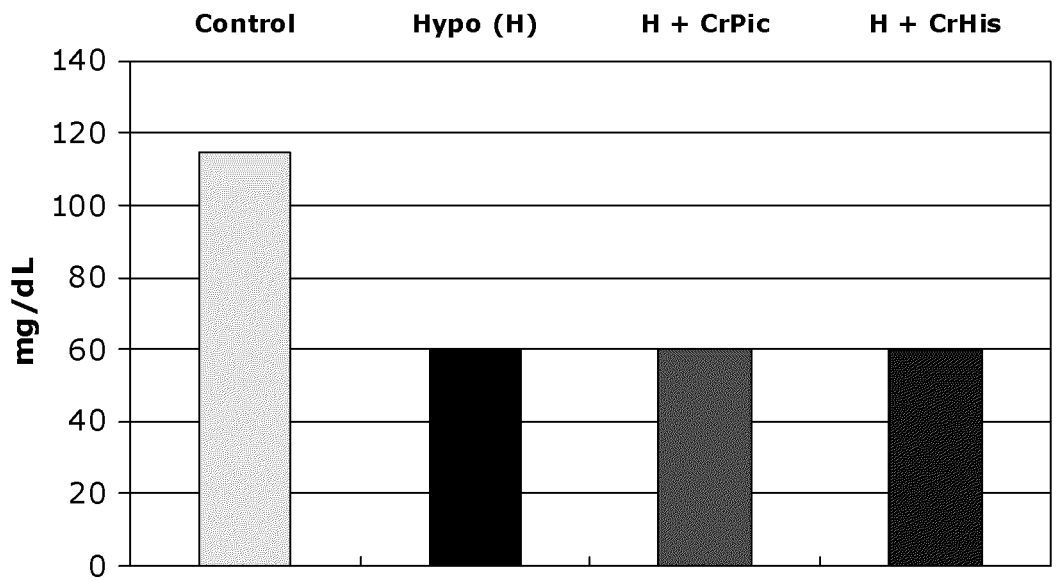
FIG. 1 is a bar graph showing serum glucose levels 0.5 hours after an insulin injection, for control (no insulin) and treatment groups, as described in Example 1. One treatment group was administered only insulin ("Hypo" or "H"). Another treatment group was administered insulin and chromium picolinate ("H+CrPic"). The final group was administered insulin and chromium histidinate ("H+CrHis").

The embodiments disclosed herein are based, in part, upon Applicant's discovery of the unexpected protective effect of chromium in preventing hypoglycemia, and in preventing or ameliorating hypoglycemia associated conditions, such as brain injury and the like, as well as Applicant's discovery of improved methods of administering insulin therapy to those in need thereof.

Chromium

As used herein, the term "chromium" refers to chromium chloride, chromium yeasts, as well as chromium complexes. Some chromium complexes useful in the embodiments disclosed herein include, but are not limited to, the following: chromium histidinate; chromium trihistidinate; chromium polyhistidinate; chromium dinicocysteinate; chromium dinicotinate tryptophan; chromium dinicotinate tyrosine; chromium dinicotinate hydroxycitrate; chromium dinicotinate cinnamate; chromium dinicotinate gallate; chromium dinicotinate 5-hydroxytryptophan; chromium dinicotinate aspartate; chromium dinicotinate glutamate; chromium dinicotinate arginate; chromium tris(tryptophan); chromium nicotinate, chromium polynicotinate; chromium picolinate; chromium monopicolinate; chromium dipicolinate; chromium tripicolinate; chromium triphenylalanine; chromium tris(tyrosine); chromium tris(hydroxycitrate); chromium tris (5-hydroxytryptophan); chromium tris(cinnamate); chromium tris(gallate); chromium complexes disclosed herein are chromium having three different carboxylate ligands. By varying ligands from nicotinic acid, glutamate, cysteinate, aspartate, argininate, tyrosine and tryptophan, at least 30 possible chromium complexes can be produced.

In various cases, the ligand(s) has/have the ability to bond to chromium via its carboxylate functional group as well as through pi electron-d orbital interaction. This secondary interaction between the ligand and chromium can increase the bioavailability and absorption of chromium.

In some embodiments, the chromium can be in the form of complexes of trivalent chromium and at least one and no more than three tyrosine or tryptophan ligands. In specific embodiments, the chromium can be in the form of chromium complexes such as chromium (III) tris(tryptophan) and chromium (III) tris(tyrosine).

In some embodiments, the chromium complexes can be complexes of trivalent chromium and one or more compounds extracted from plants. Non-limiting examples of plants from which these compounds can be extracted include plants such as genus *Garcinia, Groffonia simplicifolia*, cinnamon bark, gallnuts, sumac, witch hazel, tea leaves, and oak bark. For example, in some embodiments, chromium can be provided in the form of chromium hydroxycitrate, chromium hydroxytryptophan, chromium cinnamate, and chromium gallate.

Preferably, the chromium is provided as a combination of chromium picolinate and chromium histidinate, or as a combination of chromium nicotinate and chromium histidinate. In some preferred embodiments, the chromium is provided as chromium histidinate.

While the chromium complexes aid in the absorption of chromium by intestinal cells, in some embodiments, uncomplexed chelating agents are advantageously included in the compositions to facilitate absorption of other ingested chromium as well as other metals including, but not limited to, copper, iron, magnesium, manganese, and zinc. Suitable chelating agents include histidine, any essential amino D or L amino acids, tri amino acid formulae including but not limited to, triphenylalanine, tri histidine, tri arginine, picolinic acid, nicotinic acid, or both picolinic acid and nicotinic acid.

Chelating agents such as histidine, picolinic acid and nicotinic acid are available from many commercial sources, including Sigma-Aldrich (St. Louis, Mo.) (picolinic acid; catalog No. P5503; nicotinic acid; catalog No. PN4126). In some embodiments, the ratio of the chromium complex to the chelating agent in the embodiments disclosed herein can be from about 10:1 to about 1:10 (w/w), more preferably from about 5:1 to about 1:5 (w/w), e.g., 5:1, 5:2, 5:3, 5:4, 1:1; 1:2, 1:3, 1:4, 1:5, or any number in between. Alternatively, the molar ratio of chromium complex to the uncomplexed chelating agent is preferably 1:1, and can be from about 5:1 to about 1:10, e.g., e.g., 5:1, 5:2, 5:3, 5:4, 1:1; 1:2, 1:3, 1:4, 1:5, 1:6, 1:7, 1:8, 1:9, 1:10, or any number in between. The chelating agents with D or L amino acid and or with tri or mono and di forms of chromium complex with tri amino acid or one or more amino acids but not limited to chromium triphenylanine, chromium trihistidine, chromium poly phenylanine, chromium poly hisitidine, chromium polynicotinate, chromium di phenylananine, chromium di picolinic acid, chromium di hisitidine etc.

Some embodiments provide compositions and methods of treating subjects with compositions that comprise or consist of a therapeutically effective amount of chromium. Some embodiments provide compositions and methods of treating subjects with compositions that comprise, consist essentially of, or consist of a therapeutically effective amount of insulin. Some embodiments provide compositions and methods of treating subjects with compositions that comprise, consist essentially of, or consist of a therapeutically effective amount of chromium and a therapeutically effective amount of insulin. For example, some embodiments provide compositions and method of treating subjects that comprises, consists essentially of, or consist of a chromium-insulin complex. Various methods of treatment are discussed below.

A "therapeutically effective amount" as used herein includes within its meaning a non-toxic but sufficient amount of a compound active ingredient or composition comprising the same for use in the embodiments disclosed herein to provide the desired therapeutic effect. The exact amount of the active ingredient disclosed herein required will vary from subject to subject depending on factors such as the species being treated, the age and general condition of the subject, the severity of the condition being treated, the particular agent being administered, the weight of the subject, and the mode of administration and so forth. Thus, it is not possible to specify an exact "effective amount". However, for any given case, an appropriate "effective amount" may be determined by one of ordinary skill in the art using only routine methods.

By way of example, a "therapeutically effective amount" of the chromium disclosed herein can be, for example, 0.001 μg/kg, 0.01 μg/kg, 0.1 μg/kg, 0.5 μg/kg, 1 μg/kg, 1.5 μg/kg, 2.0 μg/kg, 2.5 μg/kg, 3.0 μg/kg, 3.5 μg/kg, 4.0 μg/kg, 4.5 μg/kg, 5.0 μg/kg, 10 μg/kg, 15 μg/kg, 20 μg/kg, 25 μg/kg, 30 μg/kg, 35 μg/kg, 40 μg/kg, 45 μg/kg, 50 μg/kg, 55 μg/kg, 60 μg/kg, 65 μg/kg, 70 μg/kg, 75 μg/kg, 80 μg/kg, 85 μg/kg, 90 μg/kg, 95 μg/kg, 100 μg/kg, 150 μg/kg, 200 μg/kg, 250 μg/kg, 300 μg/kg, 350 μg/kg, 400 μg/kg, 450 μg/kg, 500 μg/kg, 550 μg/kg, 600 μg/kg, 650 μg/kg, 700 μg/kg, 750 μg/kg, 80 μg/kg 0, 850 μg/kg, 900 μg/kg, 1 mg/kg, 1.5 mg·kg, 2.0 mg/kg, 2.5 mg/kg, 3 mg/kg, 4.0 mg/kg, 5.0 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 125 mg/kg, 150 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1 g/kg, 5 g/kg, 10 g/kg, or more, or any fraction in between of chromium. Accordingly, in some embodiments, the dose of chromium in compositions disclosed herein can be about 0.001 μg to about 100 g, preferably per day. For example, the amount of chromium can be 0.001 μg, 0.01 μg, 0.1 μg, 0.2 μg, 0.3 μg, 0.4 μg, 0.5 μg, 0.6 μg, 0.7 μg, 0.8 μg, 0.9 μg, 1 μg, 2 μg, 3 μg, 4 μg, 5 μg, 6 μg, 7 μg, 8 μg, 9 μg, 10 μg, 15 μg, 20 μg, 25 μg, 30 μg, 35 μg, 40 μg, 45 μg, 50 mg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, 20 g, 30 g, 40 g, 50 g, 60 g, 70 g, 80 g, 90 g, 100 g, or more, or any range or amount in between any two of the preceding values. The exemplary therapeutically effective amounts listed above, can, in some embodiments be administered in the methods described elsewhere herein on an hourly basis, e.g., every one, two, three, four, five, six, seven, eight, nine, ten, eleven, twelve, thirteen, fourteen, fifteen, sixteen, seventeen, eighteen, nineteen, twenty, twenty-one, twenty-two, twenty-three hours, or any interval in between, or on a daily basis, every two days, every three days, every four days, every five days, every six days, every week, every eight days, every nine days, every ten days, every two weeks, every month, or more or less frequently, as needed to achieve the desired therapeutic effect.

In some embodiments, a therapeutically effective amount of chromium is an amount that will reduce elevated blood glucose levels, but also protects against hypoglycemia (e.g., reduced high glucose levels until they go down to normal, but the chromium does not enhance any further reduction below normal). In some embodiments, the compositions disclosed herein, e.g., compositions that comprise a chromium-insulin complex, can be administered to a subject 1 time, 2 times, 3 times, 4 times 5 times, 6 times, 7 times, 8 times, 9 times, 10 times, or more, per day, for a period of time, such as 1 day, 2 days, 3 days, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 2 months, 3 months, 4 months, 5 months, 6 months, 7 months, 8 months, 9 months, 10 months, 11 months, 1 year, or more, or any amount of time in between the preceding values.

In some embodiments, the compositions described herein, for example compositions that comprise chromium and insulin, e.g., a chromium-insulin complex, can be administered to a subject per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Insulin

As used herein, "insulin" refers to insulin from a variety of sources. Naturally occurring insulin and structurally similar bioactive equivalents (insulin analogues including short acting and analogues with protracted action) can be used. Insulin useful in the embodiments disclosed herein can be isolated from different species of mammal. For example, in some embodiments, animal insulin preparations extracted from bovine or porcine pancreas can be used. In some embodiments, insulin analogues, derivatives and bioequivalents thereof can also be used. In addition to insulin isolated from natural sources, the embodiments disclosed herein can use insulin chemically synthesizing using protein chemistry techniques such as peptide synthesis. In some embodiments, analogues of insulin are also suitable.

The insulin used in the embodiments disclosed herein may be obtained by isolating it from natural sources or by chemically synthesizing it using peptide synthesis, or by using the techniques of molecular biology to produce recombinant insulin in bacteria or eukaryotic cells. The physical form of insulin may include crystalline and/or amorphous solid forms. In addition, dissolved insulin may be used. Synthetic forms of insulin are described in U.S. Pat. Nos. 4,421,685, 5,474,978, and 5,534,488, the disclosure of each of which is hereby expressly incorporated by reference in its entirety.

In some embodiments, the compositions provided herein comprise, consist essentially of, or consist of a combination of a therapeutically effective amount of insulin and a therapeutically effective amount of chromium. As discussed above, the exact amount of the chromium and/or insulin will vary from subject to subject depending on factors such as the species being treated, the age and general condition of the subject, the severity of the condition being treated, the particular agent being administered, the weight of the subject, and the mode of administration, and so forth. Thus, it is not possible to specify an exact "therapeutically effective amount". However, for any given case, an appropriate "therapeutically effective amount" may be determined by one of ordinary skill in the art using only routine methods. Exemplary dosage forms and therapeutically effective amounts of insulin useful in the embodiments disclosed herein are described in, e.g. U.S. Pat. Nos. 7,429,564 and 7,112,561, U.S. Patent Application Pub. No. 2010/0262434, and the like, each of which is hereby expressly incorporated by reference in its entirety.

By way of example, a "therapeutically effective amount" of the insulin disclosed herein can be, for example, 0.01 units of insulin, 0.1 units of insulin, 1 unit of insulin, 1.5 units of insulin, 2 units of insulin, 3 units of insulin, 4 units of insulin, 5 units of insulin, 6 units of insulin, 7 units of insulin, 8 units of insulin, 9 units of insulin, 10 units of insulin, 11 units of insulin, 12 units of insulin, 13 units of insulin, 14 units of insulin, 15 units of insulin, 16 units of insulin, 17 units of insulin, 18 units of insulin, 19 units of insulin, 20 units of insulin, 21 units of insulin, 22 units of insulin, 23 units of insulin, 24 units of insulin, 25 units of insulin, 26 units of insulin, 27 units of insulin, 28 units of insulin, 29 units of insulin, 30 units of insulin, 35 units of insulin, 40 units of insulin, 45 units of insulin, 50 units of insulin, 60 units of insulin, 70 units of insulin, 80 units of insulin, 90 units of insulin, 100 units of insulin, 150 units of insulin, 200 units of insulin, 250 units of insulin, 300 units of insulin, 400 units of insulin, 500 units of insulin, 1000 units of insulin, 2000 units of insulin, or more, or less, or any fraction in between.

Conventional administration of insulin is accomplished parenterally (e.g. intramuscularly, subcutaneously, intraperitoneal, etc.), however, there are numerous other methods of administration available that are useful in the embodiments disclosed herein. U.S. Pat. No. 5,858,968, the entire contents of which are hereby expressly incorporated herein by reference, describes the administration of insulin orally, enterally (direct incubation into the stomach), or in an aerosol, i.e., pulmonarily. U.S. Pat. No. 7,291,591, the entire contents of which are hereby expressly incorporated herein by reference, describes the administration of insulin transdermally. U.S. Pat. No. 4,164,573, the entire contents of which are hereby expressly incorporated herein by reference, describes the administration of insulin rectally. U.S. Pat. No. 5,053,389, the entire contents of which are hereby expressly incorporated herein by reference, describes various non-parenteral means of administration of insulin, including ophthalmically (citing Danish Patent No. 135,268, the entire contents of which are hereby expressly incorporated herein by reference). In some embodiments, the composition disclosed herein can be formulated for nasal administration, e.g., via an atomizer or the like.

Parenteral Administration of Insulin

U.S. Patent Application Pub. No. 2010/0262434, the entire contents of which are hereby expressly incorporated by reference, describes the process for determining the proper dose of injected insulin for a given patient. There are a number of factors that make the administration of a proper insulin dose difficult. First, injected insulin does not impact blood glucose instantly. Even fast acting insulin formulations take hours to have a biological effect. As such, conservative dosing can produce hours of high glucose before supplemental injections can be applied to reduce the glucose concentration. Overdosing can result in hypoglycemia, which presents risk of acute incapacitation or coma.

Second, a varied diet requires a concomitant adjustment in insulin dosage. The carbohydrates present in some foods is rapidly converted to glucose. The correct insulin dose, measured in units, U, necessary for the body to utilize the glucose from the carbohydrate component of a meal, $I_C$, is proportional to the carbohydrate intake, Carbs:

$$I_C = Carbs/CIR$$

Where CIR, the carbohydrate to insulin sensitivity factor, is particular for each patient and may vary depending upon a patient's condition.

Third, when the blood glucose level, BG, is not near a patient's target glucose level, $BG_T$, before a meal begins or at a time after all injected insulin has been utilized, adjustments (in the form of insulin or food depending on the direction of deviation) should be administered to correct for the deviation. The amount of insulin adjustment for high blood glucose deviations, $I_B$, depends on the patient's individual insulin sensitivity factor, ISF.

$$I_B = (BG - BG_T)/ISF$$

$I_B$ can be positive if BG is higher than the target or negative if BG is lower than the target. If positive, a dosage of insulin $I_B$ should return the patient near to their target blood glucose level. If $I_B$ is negative, the current blood glucose (BG) is below the target, so the adjustment would need to involve food ingestion.

Fourth, if $I_B$ is negative, food can be consumed to effect an adjustment. Ideally, the amount of food would be just enough to correct the low BG. A food intake sensitivity factor can be used to guide the food intake. Basing the food intake on the food carbohydrate content is currently a preferred method. The recommended carbohydrate intake, Carbs, to correct for a given blood glucose negative deviation, $BG - BG_T$ is:

$$Carbs = -CIR/ISF*(BG - BG_T)$$

−CIR/ISF, is also known as 1/CGR, and can be calculated if one has estimates for their CIR and ISF.

Fifth, the patient's sensitivity factors can be a function of their condition. So, exercise, stress, illness, etc. can be sources of variation that change how the patient is utilizing insulin. Over longer time periods, the patient's weight and progressing conditions can impact the sensitivity factors.

The ISF (insulin sensitivity factor) is the amount by which an individual patient's blood glucose concentration is reduced for each unit of rapid insulin taken. ISFs are generally in the range of 30 to 50 mg/dL/U.

Oral Administration of Insulin

The oral administration of insulin is described in U.S. Pat. No. 7,429,564, hereby expressly incorporated by reference in its entirety. Oral administration of insulin requires consideration of the same factors affecting the parenteral administration of insulin, in addition to factors specific to oral administration, including, for example, the chemical structure of the particular delivery agent, the nature and extent of interaction of insulin and the delivery agent, the nature of the unit dose; the concentration of delivery agent in the gastrointestinal tract, and the ratio of delivery agent to insulin. The nature of the unit dose for oral administration can be, but is not limited to, solid, liquid, tablet, capsule, suspension, or other acceptable dosage forms. The means of delivery of the pharmaceutical composition (for example, a composition comprising chromium and insulin, e.g., a composition comprising a chromium-insulin complex), can be, but is not limited to, for example, a capsule, compressed tablet, pill, solution, gel, freeze-dried powder ready for reconstitution, suspension suitable for administration to the subject, or other means.

Typically, insulin is not absorbed through the gastrointestinal tract. However, there are several delivery agents that make insulin bioavailable and absorbable through the gastrointestinal mucosa when orally administered. By way of example, an acceptable delivery agent can include, a compound of the formula or a pharmaceutically effective salt thereof:

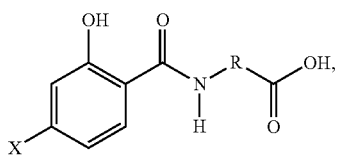

wherein X is hydrogen or halogen; and R is substituted or unsubstituted $C_1$-$C_3$ alkylene, substituted or unsubstituted $C_1$-$C_3$ alkenylene, substituted or unsubstituted $C_1$-$C_3$ alkyl (arylene), or substituted or unsubstituted $C_1$-$C_3$ aryl (alkylene). The acceptable delivery agents also include, but are not limited to, a compound of the formula above or a pharmaceutically effective salt thereof wherein: X is a hydrogen or halogen; and R is substituted or unsubstituted $C_1$-$C_{12}$ alkylene, or substituted or unsubstituted $C_1$-$C_{12}$ alkenylene. The acceptable delivery agents also include, but are not limited to, a compound of the formula above or a pharmaceutically effective salt thereof wherein X is chlorine and R is $C_3$ alkylene. Acceptable insulin delivery agents can also include a compound of the formula or a pharmaceutically effective salt thereof:

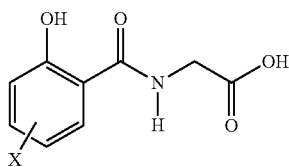

wherein X is one or more of hydrogen, halogen, hydroxyl, or $C_1$-$C_3$ alkoxy; and R is substituted or unsubstituted $C_1$-$C_3$ alkylene, or substituted or unsubstituted $C_1$-$C_3$ alkenylene. The acceptable delivery agents also include the compound 4-[(4-chloro, 2-hydroxybenzoyl)amino]butanoic acid (alternatively known as N-(4-chlorosalicyloyl)-4-aminobutyrate, or by the short name "4-CNAB"), as well as the monosodium salt thereof.

In some embodiments, the delivery agents can be in the form of the carboxylic acid or salts thereof. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethyl amine or pyridine. Preferably, the salts are sodium salts. The salts may be mono- or multi-valent salts, such as monosodium salts and di-sodium salts. The salts may also be solvates, including ethanol solvates, and hydrates.

Other suitable delivery agents that can be used for oral administration of insulin include those delivery agents described U.S. Pat. Nos. 5,650,386, 5,773,647, 5,776,888, 5,804,688, 5,866,536, 5,876,710, 5,879,681, 5,939,381, 5,955,503, 5,965,121, 5,989,539, 5,990,166, 6,001,347, 6,051,561, 6,060,513, 6,090,958, 6,100,298, 5,766,633, 5,643,957, 5,863,944, 6,071,510 and 6,358,504, each of which is hereby expressly incorporated by reference in its entirety. Additional suitable delivery agents are described in International Publications Nos. WO 01/34114, WO 01/21073, WO 01/41985, WO 01/32130, WO 01/32596, WO 01/44199, WO 01/51454, WO 01/25704, WO 01/25679, WO 00/50386, WO 02/02509, WO 00/47188, WO 00/07979, WO 00/06534, WO 98/25589, WO 02/19969, WO 00/59863, WO 95/28838, WO 02/20466, WO 02/19969, WO 02/069937, and WO 02/070438, each of which is hereby expressly incorporated by reference in its entirety.

The insulin dose for oral administration is typically higher than for parenteral administration. The preferred amount of orally administered insulin varies from subject to subject, and can be determined by one skilled in the art, taking into consideration factors such as the species being treated, the age and general condition of the subject, co-morbidities, the severity of the condition being treated, type of insulin being administered, the weight of the subject, the delivery agent used, and so on.

Other Modes of Administration of Insulin

U.S. Pat. No. 7,112,561, hereby expressly incorporated by reference in its entirety, describes compositions and methods for delivery of insulin other than by injection, across skin, and membranes of various body cavities such as ocular, nasal, oral, buccal, anal, rectal, vaginal, blood-brain barrier, and like membranes. Administration of insulin through skin membranes and membranes of body cavities requires consideration of the same factors affecting the parenteral administration of insulin, in addition to other factors specific to administration through skin membranes and/or membranes of body cavities, including, but not limited to: the chemical structure of the particular delivery agent; the nature and extent of interaction of insulin and the delivery agent; the nature of the unit dose; the concentration of delivery agent, and, the ratio of delivery agent to insulin. The nature of the unit dose for oral administration can be, but is not limited to, solid, liquid, tablet, capsule, or suspension. The means of delivery of the pharmaceutical composition can be, but is not limited to, for example, a capsule, compressed tablet, pill, solution, freeze-dried, lotion, foam, aerosol, cream, gel, or powder ready for reconstitution or suspension suitable for administration to the subject.

The delivery agent for administration through skin membranes or membranes of body cavities can include permeation enhancers to facilitate delivery of insulin through the membranes. The acceptable permeation enhancers can include compounds having the following structure:

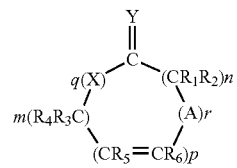

wherein X and Y are oxygen, sulfur or an imino group of the structure:

or =N—R with the proviso that when Y is the imino group, X is an imino group, and when Y is sulfur, X is sulfur or an imino group, A is a group having the structure:

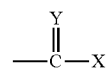

wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$, and $R_6$ is independently hydrogen or an alkyl group having from 1 to 6 carbon atoms which may be straight chained or branched provided that only one of R, to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are 0, then m+n is at least 11. Preferably, the permeation enhancer defined above is combined in a composition with a therapeutically effective amount of insulin and a liquid carrier, said composition having an acidic pH. In general, the pH of the composition is at least 2 and no greater than 4.5. Preferably, the pH is: no greater than 4. More preferably, the pH is in the rage of 2.5 to 3.8. Even more preferably, the pH is about 3.

Other suitable permeation enhancers are described in U.S. Pat. Nos. 5,023,252, and 5,731,303 which are hereby expressly incorporated by reference in its entirety.

Although the above are preferred permeation enhancers, one of ordinary skill in the art would recognize that the instant teachings would also be applicable to other permeation enhancers. Non-limiting examples of other permeation enhancers useful in the embodiments disclosed herein are the simple long chain esters that are Generally Recognized As Safe (GRAS) in the various pharmacopoeial compendia. These may include simple aliphatic, unsaturated or saturated (but preferably fully saturated) esters, which contain up to medium length chains. Non-limiting examples of such esters include isopropyl myristate, isopropyl palmitate, myristyl myristate, octyl palmitate, and the like. The enhancers are of a type that are suitable for use in a pharmaceutical composition. The artisan of ordinary skill will also appreciate that those materials that are incompatible with or irritating to mucous membranes should be avoided.

The enhancer can be present in the composition in a concentration effective to enhance penetration of the insulin, to be delivered, through the membrane. Various considerations should be taken into account in determining the amount of enhancer to use. Such considerations include, for example, the amount of flux (rate of passage through the membrane) achieved and the stability and compatibility of the components in the formulations. The enhancer is generally used in an amount of about 0.01 to about 25 wt. % the composition, more generally in an amount of about 0.1 to about 15 wt. % the composition, and in preferred embodiments in an amount of about 0.5 to about 15 wt % the composition.

The liquid carrier is present in the composition in a concentration effective to serve as a suitable vehicle for the compositions of the embodiments disclosed herein. In general, the carrier can be used in an amount of about 40 to about 98 wt. % of the composition and in preferred embodiments in an amount of about 50 to about 98 wt. % of the composition.

In general, compositions that contain insulin can be stored in a refrigerator. However, refrigeration may result in crystallization of the permeation enhancer. In order to inhibit or prevent such crystallization, in a preferred embodiment the composition includes one or more crystallization inhibitors to inhibit the crystallization of the permeation enhancer. Crystallization, if allowed to proceed, renders the emulsion unstable and has an adverse effect on shelf life. Preferred crystallization inhibitors function by lowering the temperature at which the involved compound crystallizes. Examples of such crystallization inhibitors include natural oils, oily substances, waxes, esters, and hydrocarbons. Examples of natural oils or oily substances include Vitamin E acetate, octyl palmitate, sesame oil, soybean oil, safflower oil, avocado oil, palm oil, and cottonseed oil. The selection of a suitable crystallization inhibitor is deemed to be within the scope of those skilled in the art from the teachings herein. Preferred crystallization inhibitors function by lowering the temperature at which the permeation enhancer crystallizes.

Inhibitors which are capable of lowering the temperature of crystallization of the involved compound to below about 25° C., are particularly preferred, with those capable of lowering the crystallization of the involved compound to below about 5° C. being especially preferred. Examples of especially preferred crystallization inhibitors for use in inhibiting the crystallization of oxacyclohexadecan-2-one include hexadecane, isopropyl myristate, octyl palmitate, cottonseed oil, safflower oil, and Vitamin E acetate, each of which may be used in pharmaceutical preparations.

The crystallization inhibitor is present in the composition in a concentration effective to inhibit the crystallization of the permeation enhancer. In general the crystallization inhibitor is present in an amount of about 0.001 to about 5 wt. % the composition, more generally in an amount of from about 0.01 to about 2 wt % the composition. In one embodiment the crystallization inhibitor is present in an amount of from about 0.1 to about 1 wt. % of the composition. The crystallization inhibitor is one preferably used when the enhancer has a crystallization temperature above about 0° C. In particular, for example, a crystallization inhibitor is preferably used when the enhancer is, pentadecalactone and/or cyclohexadecanone, since these crystallize above room temperature.

Compositions Comprising Chromium and Insulin

Zinc ions have been reported exert a stabilizing effect on insulin solutions. See, e.g., U.S. Pat. No. 4,476,118, incorporated by reference it its entirety. For example, including two to five zinc ions per hexamer of insulin may help prevent insulin precipitation. In contrast to the Zn-insulin complexes described, in U.S. Pat. No. 4,476,118, the chromium-insulin complexes provide favorable absorption and therapeutic effects.

In some embodiments, chromium is provided in combination with insulin, e.g., within a single dosage form, such as a single injectable dosage form or a single oral dosage form. In some embodiments, chromium is provided with insulin in a multi-unit dosage form. In some embodiments, chromium is provided dissolved in an insulin solution. In other embodiments, chromium is provided in suspension in an insulin solution. Accordingly, provided herein are compositions that comprise, consist essentially of, or consist of chromium and insulin. In some embodiments, the compositions comprise a chromium-insulin complex.

In some embodiments, the compositions provided herein include a combination of insulin and chromium, e.g., within in a single dosage form, and are formulated for intradermal, intramuscular, intraperitoneal, intravenous, subcutaneous, intranasal, epidural, oral, sublingual, intranasal, intracerebral, intravaginal, transdermal, rectal, ophthalmic, or topical delivery. In some embodiments, chromium is provided with insulin in a multi-unit dosage form. In some embodiments, chromium is provided in suspension in an insulin solution. Intranasal delivery may be accomplished with an atomizer. The preferred mode of administration is left to the discretion of the practitioner, and will depend in part upon the site of the medical condition. The effective amounts of chromium, insulin, and or chromium-insulin complex can vary depending on the route of administration. In most instances, administration will result in the release of the compounds of the embodiments disclosed herein into the bloodstream. Accordingly, provided herein are compositions that comprise, consist essentially of, or consist of chromium and insulin, for example, in the form of a chromium-insulin complex.

In some embodiments, the compositions provided herein comprise, consist essentially of, or consist of a combination of a therapeutically effective amount of insulin and a therapeutically effective amount of chromium. In some embodiments, these compositions can comprise, consist essentially of, or consist of a chromium-insulin complex. In some embodiments, the compositions provided herein comprise, consist essentially of, or consist of a combination of a synergistically effective amount of insulin and a synergistically effective amount of chromium. In some embodiments, the se compositions can comprise, consist essentially of, or consist of a chromium insulin complex. In some embodiments, the compositions provided herein comprise chromium that is dissolved in a solution of insulin. In some embodiments, the se compositions can comprise, consist essentially of, or consist of a chromium insulin complex. In other embodiments, the compositions provided herein comprise chromium that is suspended in a solution of insulin. In some embodiments, the se compositions can comprise, consist essentially of, or consist of a chromium insulin complex.

In some embodiments, the compositions provided herein include an injectable solution comprising a combination of a therapeutically effective amount of chromium and a therapeutically effective amount of insulin. In some embodiments, the combination of chromium and insulin results in chemical structures that have benefits for the treatment of diabetes, including but not limited to increased rate of absorption and overall absorption of insulin, decreased insulin dissolution rate, increased receptor binding, and therapeutic properties. In some embodiments, the combination of chromium and insulin reduces serum glucose levels at a faster rate than insulin alone.]

Chromium-Insulin Complexes

In some embodiments, the chromium and insulin compositions provided herein comprise, consist essentially of, or consist of a chromium-insulin complex. In some embodiments, the chromium-insulin complex comprise a stoichiometric ratio of chromium to insulin, e.g., 1:1, 2:1, 3:1, 4:1, 5:1, 6:1, 7:1, 8:1, 9:1 or 10:1. In some embodiments, the chromium and insulin are present in the chromium insulin complexes in non-stoichiometric amounts, e.g., between 1 and 10 molecules of chromium (e.g., chromium complex), per insulin hexamer. In some embodiments the complex has a molecular weight that is between about 30 and 40 kDa, e.g., 30 kDa, 31 kDa, 32 kDa, 33 kDa, 34 kDa, 35 kDa, 36 kDa, 37 kDa, 38 kDa, 39 kDa, 40 kDa, or more.

In some embodiments, the chromium-insulin complex provides a therapeutically effective amount of chromium and insulin. In some embodiments, the composition comprises, consists essentially of, or consists of isolated and/or purified amounts of a chromium-insulin complex. The isolated and/or purified amounts of a chromium-insulin complex can be provided in amounts to provide a therapeutically effect amount of chromium and/or insulin. In some embodiments, the chromium-insulin complex is not isolated and/or purified, but rather is present within a mixture of chromium and insulin.

In some embodiments, chromium and/or insulin are provided with a nutritionally acceptable carrier or a pharmaceutically acceptable carrier. As used herein, the phrase "nutritionally acceptable carrier", "nutritionally acceptable excipient", "pharmaceutically acceptable carrier", or "pharmaceutically acceptable excipient" refers to nutritionally or pharmaceutically acceptable materials, compositions or vehicles, suitable for administering compounds of the embodiments disclosed herein to mammals. The carriers can include liquid or solid filler, diluent, excipient, solvent or encapsulating material, involved in carrying or transporting the subject agent from one organ, or portion of the body, to another organ, or portion of the body. Carriers can be "acceptable" in the sense of being compatible with the other ingredients of the formulation and not injurious to the patient. Some examples of materials which can serve as nutritionally or pharmaceutically acceptable carriers include, but are not limited to: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients; such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. In some embodiments, the nutritionally or pharmaceutically acceptable carrier can be suitable for intravenous administration. In some embodiments, the nutritionally or pharmaceutically acceptable carrier can be suitable for locoregional injection.

The language "pharmaceutical composition" is used interchangeably with "therapeutic agent" and includes preparations suitable for administration to mammals, e.g., humans. When the compounds of the embodiments disclosed herein are administered as pharmaceuticals to mammals, e.g., humans, they can be given per se or as a pharmaceutical composition containing, for example, 0.1 to 99.5% (more preferably, 0.5 to 90%) of active ingredients in combination with a nutritionally or pharmaceutically acceptable carrier. The amount of therapeutic agents incorporated into the multiple unit dosage form of the embodiments disclosed herein is quantum sufficiat to achieve the desired therapeutic effect. The dosage amounts for the disclosed therapeutic agents are well-established in the arts and can be optimized for any particular indication via routine experimentation.

In another aspect, the embodiments relate to methods of treating a subject with the compositions disclosed herein. The terms "subject," "patient" or "individual" as used herein refer to a vertebrate, preferably a mammal, more preferably a human. "Mammal" can refer to any animal classified as a mammal, including humans, domestic and farm animals, and zoo, sport, or pet animals, such as, for example, horses, sheep, cows, pigs, dogs, cats, etc. Preferably, the mammal is human.

Synergistically Effective Compositions Comprising Chromium and Insulin

In some embodiments, the compositions provided herein comprise a synergistically effective amount of chromium and insulin selected together to provide a greater than additive effect. This greater than additive effect can include, but is not limited to, an increase in insulin receptor binding. A "synergistically effective amount" as used herein refers to the amount of one component of a composition necessary to elicit a synergistic effect in another component present in the composition. A "synergistic effect" as used herein refers to a result that is markedly greater than what would be expected when either component is administered alone. The exact synergistically effective amounts of the active ingredients disclosed herein required will vary from subject to subject depending on factors such as the species being treated, the age and general condition of the subject, co-morbidities, the severity of the condition being treated, the particular agents being administered, the weight of the subject, and the mode of administration, and so forth. Thus, it is not possible to specify an exact "synergistic amount". However, for any given case, an appropriate "synergistically effective amount" may be determined by one of ordinary skill in the art using routine methods.

By way of example, a "synergistically effective amount" of the chromium, e.g., present in the form of a chromium complex, disclosed herein can be, for example 0.001 μg/kg, 0.01 μg/kg, 0.1 μg/kg, 0.5 μg/kg, 1 μg/kg, 1.5 μg/kg, 2.0 μg/kg, 2.5 μg/kg, 3.0 μg/kg, 3.5 μg/kg, 4.0 μg/kg, 4.5 μg/kg, 5.0 μg/kg, 10 μg/kg, 15 μg/kg, 20 μg/kg, 25 μg/kg, 30 μg/kg, 35 μg/kg, 40 μg/kg, 45 μg/kg, 50 μg/kg, 55 μg/kg, 60 μg/kg, 65 μg/kg, 70 μg/kg, 75 μg/kg, 80 μg/kg, 85 μg/kg, 90 μg/kg, 95 μg/kg, 100 μg/kg, 150 μg/kg, 200 μg/kg, 250 μg/kg, 300 μg/kg, 350 μg/kg, 400 μg/kg, 450 μg/kg, 500 μg/kg, 550 μg/kg, 600 μg/kg, 650 μg/kg, 700 μg/kg, 750 μg/kg, 80 μg/kg 0, 850 μg/kg, 900 μg/kg, 1 mg/kg, 1.5 mg·kg, 2.0 mg/kg, 2.5 mg/kg, 3 mg/kg, 4.0 mg/kg, 5.0 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 125 mg/kg, 150 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1 g/kg, 5 g/kg, 10 g/kg, or more, or any fraction in between of chromium. Accordingly, in some embodiments, the synergistically effective amount of chromium in compositions disclosed herein can be about 0.001 μg to about 1 g, preferably per day. For example, the amount of chromium, e.g., present in a chromium complex, can be 0.001 μg, 0.01 μg, 0.1 μg, 0.2 μg, 0.3 μg, 0.4 μg, 0.5 μg, 0.6 μg, 0.7 μg, 0.8 μg, 0.9 μg, 1 μg, 2 μg, 3 μg, 4 μg, 5 μg, 6 μg, 7 μg, 8 μg, 9 μg, 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 1.25 mg, 1.5 mg, 1.75 mg, 2.0 mg, 2.25 mg, 2.5 mg, 2.75 mg, 3.0 mg, 3.25 mg, 3.5 mg, 3.5 mg, 3.75 mg, 4.0 mg, 4.25 mg, 4.5 mg, 4.75 mg, 5.0 mg, 5.25 mg, 5.5 mg, 5.75 mg, 6.0 mg, 6.25 mg, 6.5 mg, 6.75 mg, 7.0 mg, 7.25 mg, 7.5 mg, 7.75 mg, 8.0 mg, 8.25 mg, 8.5 mg, 8.75 mg, 9.0 mg, 8.25 mg, 9.5 mg, 9.75 mg, 10 mg, 20 mg, 30 mg, 40 mg, 50 mg, 60 mg, 70 mg, 80 mg, 90 mg, 100 mg, 200 mg, 300 mg, 400 mg, 500 mg, 1 g, or more, or any range or amount in between any two of the preceding values.

Likewise, by way of example, a "synergistically effective amount" of insulin disclosed herein can be, for example, 0.01 units of insulin, 0.1 units of insulin, 1 unit of insulin, 1.5 units of insulin, 2 units of insulin, 3 units of insulin, 4 units of insulin, 5 units of insulin, 6 units of insulin, 7 units of insulin, 8 units of insulin, 9 units of insulin, 10 units of insulin, 11 units of insulin, 12 units of insulin, 13 units of insulin, 14 units of insulin, 15 units of insulin, 16 units of insulin, 17 units of insulin, 18 units of insulin, 19 units of insulin, 20 units of insulin, 21 units of insulin, 22 units of insulin, 23 units of insulin, 24 units of insulin, 25 units of insulin, 26 units of insulin, 27 units of insulin, 28 units of insulin, 29 units of insulin, 30 units of insulin, 35 units of insulin, 40 units of insulin, 45 units of insulin, 50 units of insulin, 60 units of insulin, 70 units of insulin, 80 units of insulin, 90 units of insulin, 100 units of insulin, 150 units of insulin, 200 units of insulin, 250 units of insulin, 300 units of insulin, 400 units of insulin, 500 units of insulin, 1000 units of insulin, 2000 units of insulin, or more, or any fraction in between.

In other embodiments, there is a range of ratios of chromium to insulin that results in the greatest synergistic effect upon the subject. The exact ratio of the active ingredients disclosed herein required will vary from subject to subject depending on factors such as the species being treated, the age and general condition of the subject, co-morbidities, the severity of the condition being treated, the particular agents being administered, the weight of the subject, and the mode of administration, and so forth. Thus, it is not possible to specify an exact ratio or range of ratios. However, for any given case, an appropriate ratio or range of ratios may be determined by one of ordinary skill in the art using only routine methods.

By way of example, the ratio of chromium to insulin disclosed herein can be, for example, 0.0001 μg chromium/unit insulin, 0.001 μg chromium/unit insulin, 0.002 μg chromium/unit insulin, 0.003 μg chromium/unit insulin, 0.004 μg chromium/unit insulin, 0.005 μg chromium/unit insulin, 0.006 μg chromium/unit insulin, 0.007 μg chromium/unit insulin, 0.008 μg chromium/unit insulin, 0.009 μg chromium/unit insulin, 0.01 μg chromium/unit insulin, 0.02 μg chromium/unit insulin, 0.03 μg chromium/unit insulin, 0.04 μg chromium/unit insulin, 0.05 μg chromium/unit insulin, 0.06 μg chromium/unit insulin, 0.07 μg chromium/unit insulin, 0.08 μg chromium/unit insulin, 0.09 μg chromium/unit insulin, 0.10 μg chromium/unit insulin, 0.11 μg chromium/unit insulin, 0.12 μg chromium/unit insulin, 0.13 μg chromium/unit insulin, 0.14 μg chromium/unit insulin, 0.15 μg chromium/unit insulin, 0.16 μg chromium/unit insulin, 0.17 μg chromium/unit insulin, 0.18 μg chromium/unit insulin, 0.19 μg chromium/unit insulin, 0.2 μg chromium/unit insulin, 0.3 μg chromium/unit insulin, 0.4 μg chromium/unit insulin, 0.5 μg chromium/unit insulin, 0.6 μg chromium/unit insulin, 0.7 μg chromium/unit insulin, 0.8 μg chromium/unit insulin, 0.9 μg chromium/unit insulin, 1 μg chromium/unit insulin, 2 μg chromium/unit insulin, 3 μg chromium/unit insulin, 4 μg chromium/unit insulin, 5 μg chromium/unit insulin, 10 μg chromium/unit insulin, 20 μg chromium/unit insulin, 50 μg chromium/unit insulin, 100 μg chromium/unit insulin, 200 μg chromium/unit insulin, 500 μg chromium/unit insulin, or more, or any fraction in between. By way of example, the range of ratios of chromium to insulin disclosed herein can be, for example, 0.001-20 μg chromium/unit insulin, 0.001-0.01 μg chromium/unit insulin 0.01-0.1 μg chromium/unit insulin, 0.1-1 μg chromium/unit insulin, 1-2 μg chromium/unit insulin, 2-3 μg chromium/unit insulin, 3-4 μg chromium/unit insulin, 4-5 μg chromium/unit insulin, 5-10 μg chromium/unit insulin, 10-20 μg chromium/unit insulin, or more, or any fraction in between.

In some embodiments, an improved method of administering insulin to a subject in need thereof is provided. This improved method comprises: combining synergistically effective amounts of insulin and chromium to create a composition; determining an optimal dosage of the composition for the subject; and, administering the optimal dosage of the composition to the subject. The optimal dosage of the composition can be determined by administering the composition to a subject, and then adjusting the insulin dosage to the lowest value that achieves the desired effect. For example, in treating diabetes, the desired effect is the stabilization of serum glucose to a level that is neither hyperglycemic nor hypoglycemic. Thus, the optimal dosage of a composition for treating diabetes is the lowest dosage that brings serum glucose to a level that is neither hyperglycemic nor hypoglycemic. Given chromium's serum glucose-stabilizing effect, the optimal dosage of a composition comprising synergistically effective amounts of insulin and chromium likely contains less insulin than would be optimal were only insulin being administered.

Kits Comprising Insulin and Chromium

In another aspect, the embodiments relate to an insulin injection kit comprising a syringe, a solution of insulin, and chromium. In some embodiments, the kit includes a chromium-insulin complex. The kit allows the end user to combine the chromium and insulin prior to administration. Thus, the end user is able to vary the dosage of chromium and insulin, as well as the ratio of chromium to insulin in a composition prior to injection. In some embodiments, the syringe included in the kit is configured to combine the insulin and chromium within the syringe itself, such as the syringe disclosed in U.S. Pat. No. 4,424,057, the disclosure of which is hereby expressly incorporated by reference in its entirety.

Methods for Making a Composition Comprising Chromium and Insulin

In another embodiment, the method for making an injectable composition of chromium and insulin disclosed herein comprises combining chromium and insulin, thereby arriving at the injectable composition. In some embodiments, the chromium component takes the form of, but is not limited to: chromium (e.g., a chromium complex) suspended in a solution; chromium (e.g., a chromium complex) dissolved in a solution; chromium (e.g., in the form of a chromium complex) in a powder; or, chromium (e.g., a chromium complex) in any form combinable with a solution of insulin. In some embodiments, the injectable composition takes the form of, but is not limited to: a suspension; a solution; or, any other composition of chromium and a solution of insulin.

Methods for Treating Overweight Subjects in Need of Insulin

In another embodiment, a method for stabilizing serum glucose levels in an overweight subject in need thereof is provided, comprising the steps of: (a) identifying an overweight subject who is in need of insulin, and, (b) administering a composition comprising chromium and insulin (e.g., in the form of a composition comprising a chromium-insulin complex) to the subject. In some embodiments, the composition may be administered parenterally, nasally, orally, or pulmonarily. In some embodiments, the overweight subject has diabetes, often Type 2 diabetes. In some embodiments, the subject has Type 1 diabetes. In other words, in some embodiments, the compositions and/or complexes described herein can be used to stabilize serum glucose levels in subjects in need thereof.

Excess body weight is one of the major risk factor for developing diabetes. Overweight people with diabetes overwhelmingly suffer from Type 2 diabetes. However, treatment of diabetes, e.g., with insulin, often results in increased body mass as a result of lowered metabolic rates and increased fat and glucose storage. This can lead to a cycle in which one's diabetes may worsen as a result of the weight gain caused by treatment, leading to the need for more treatment, resulting in more weight gain. By combining chromium and insulin, the weight gain associated with insulin treatment can be attenuated by the weight loss effects of chromium supplementation. Chromium stabilizes serum glucose levels above hypoglycemic levels, whereas insulin alone may cause excessive glucose uptake, sometimes resulting in hypoglycemia. Because chromium combined with insulin may result in less glucose uptake compared to insulin alone, less glucose can be stored, resulting in less weight gain. Likewise, because chromium works to normalize glucose metabolism, administration of chromium with insulin may act to increase a subject's body weight where the subject is underweight.

In other embodiments, a method of preventing diabetes treatment-induced weight gain is provided, comprising administering a composition comprising insulin and chromium. In some embodiments, the composition comprising insulin and chromium is administered parenterally.

Improved Method for Stabilizing Serum Glucose Levels

In another embodiment, an improved method for stabilizing serum glucose levels in a subject in need thereof is provided. The improvement comprises the steps of combining synergistically effective amounts of insulin and chromium to create a composition, and administering the composition to the subject. In some embodiments, the improved method is administered, for example, parenterally, nasally, orally, pulmonarily, or transdermally. In some embodiments, the improvement comprises providing a therapeutically effective amount of a composition comprising a chromium-insulin complex and administering the composition to the subject. In this way, the compositions described herein can be used to provide an improved method for stabilizing serum glucose levels in comparison to other known compositions.

Improved Method for Raising Serum Insulin Levels

In another embodiment, an improved method for raising serum insulin levels is provided. The improvement comprises the steps of combining synergistically effective amounts of insulin and chromium to create a composition, and administering the composition to the subject. In some embodiments, the improved method is administered, for example, parenterally, nasally, orally, pulmonarily, or transdermally. In some embodiments, the improvement comprises providing a therapeutically effective amount of a composition comprising a chromium-insulin complex and administering the complex to the subject. That is to say, the compositions described herein can be used to provide an improved method for elevating serum insulin levels in comparison to other known compositions and/or insulin alone.

Improved Method for Stabilizing Body Weight

In another embodiment, an improved method for stabilizing a subject's body weight is provided. In individuals with Type 1 diabetes, insulin therapy can result in weight loss. As shown in Example 6, below, the compositions provided herein have been shown to reduce the weight loss associated with insulin therapy in subjects with Type 1 diabetes. Individuals with Type 2 diabetes often experience weight gain. The compositions provided herein advantageously reduce weight gain associated with Type 2 diabetes. In other words, the compositions provided herein are beneficial in stabilizing weight in individuals with diabetes. The improvement comprises the steps of combining synergistically effective amounts of insulin and chromium to create a composition, and administering the composition to a subject in need thereof. In some embodiments, the improved method is administered, for example, parenterally, nasally, orally, pulmonarily, or transdermally. In some embodiments, the improvement comprises providing a therapeutically effective amount of a composition comprising a chromium-insulin complex and administering the complex to the subject. In this way, the compositions described herein can be used to provide an improved method for elevating serum insulin levels in comparison to other known compositions and/or insulin alone.

Compositions and Methods for Treatment of Other Glucose-Metabolism-Related Diseases and Disorders In another aspect, some embodiments relate to compositions for the treatment of glucose metabolism-related diseases and disorders other than hypoglycemia, and methods of using the same. The compositions for the treatment of other glucose metabolism related diseases are the same compositions described herein, including chromium, and chromium in combination with insulin. Glucose metabolism-related diseases and disorders include, but are not limited to, Alzheimer's Disease, dementia, mild cognitive impairment, attention deficit hyperactivity disorder (ADHD), Parkinson's Disease, Huntington's Disease, Amyotrophic Lateral Sclerosis (ALS), epilepsy, diabetes, hypoglycemia, and any other glucose metabolism-related diseases and disorders. Thus, the compositions and/or complexes disclosed herein may be used to treat glucose metabolism-related diseases such as Alzheimer's Disease, dementia, mild cognitive impairment, attention deficit hyperactivity disorder (ADHD), Parkinson's Disease, Huntington's Disease, Amyotrophic Lateral Sclerosis (ALS), epilepsy, diabetes, hypoglycemia.

EXAMPLES

Example 1

Chromium Reduces the Severity of Brain Damage in Insulin-Induced Hypoglycemic Rats In order to evaluate chromium's potential protective effects preventing insulin-induced hypoglycemia, animals were administered insulin to induce hypoglycemia, and markers of hypoglycemic brain damage were compared in animals with and without administration of chromium.

Briefly, hypoglycemia was induced in Sprague-Dawley rats (males, 8-weeks old) by intraperitoneal injection of 15 U insulin/kg BW. The rats were separated into four groups of 15 rats each: (1) a control group not receiving insulin ("Control"); (2) a group not administered chromium ("Hypo"); (3) a group administered 110 µg/kg/day of chromium picolinate (CrPic); and, a group administered 110 µg/kg/day of chromium histidinate (CrHis). After one week of dosing, brains were removed from the sacrificed rats and analyzed for markers of hypoglycemic damage: GLUT-1; GLUT-3; Nrf2; GFAP; and HNE. The data are shown in Table 1 and FIGS. 1-6.

As shown in FIG. 1, chromium pretreatment did not raise or lower serum glucose levels after insulin injection. These data demonstrate that chromium is useful for the normalization of serum glucose levels, i.e., as influenced by insulin administration.

Figure 2:
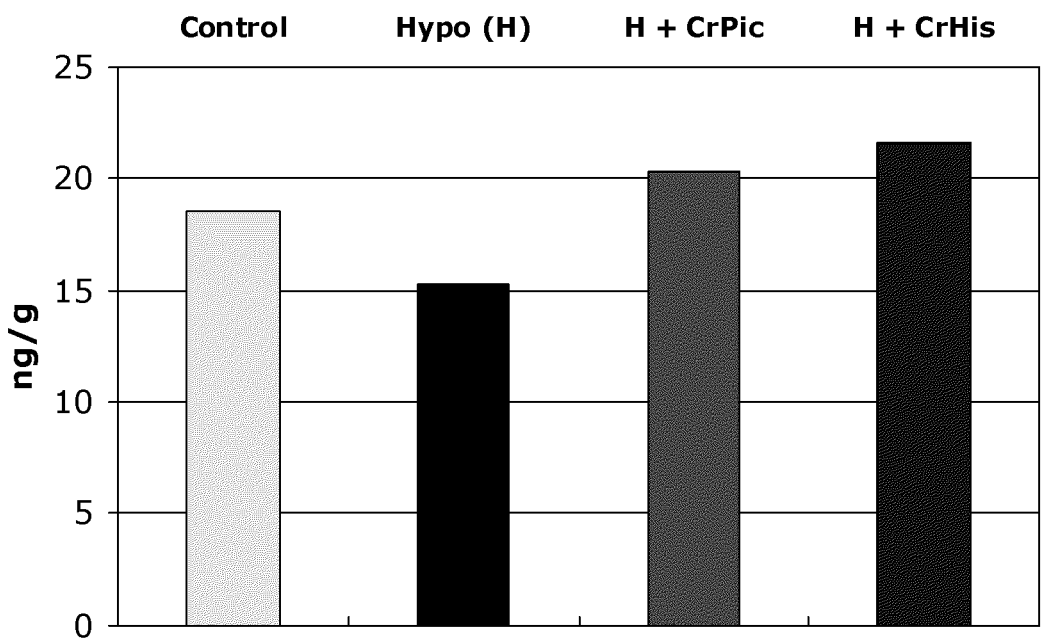
FIG. 2 is a bar graph showing brain chromium levels after treatment for control (no treatment) and treatment groups (H, H+CrPic, and H+CrHis), as described in Example 1.

As shown in FIG. 2, in non-chromium treated animals, insulin induced hypoglycemia significantly lowered brain chromium tissue levels. By contrast, chromium treatment raised brain chromium levels.

Figure 3:
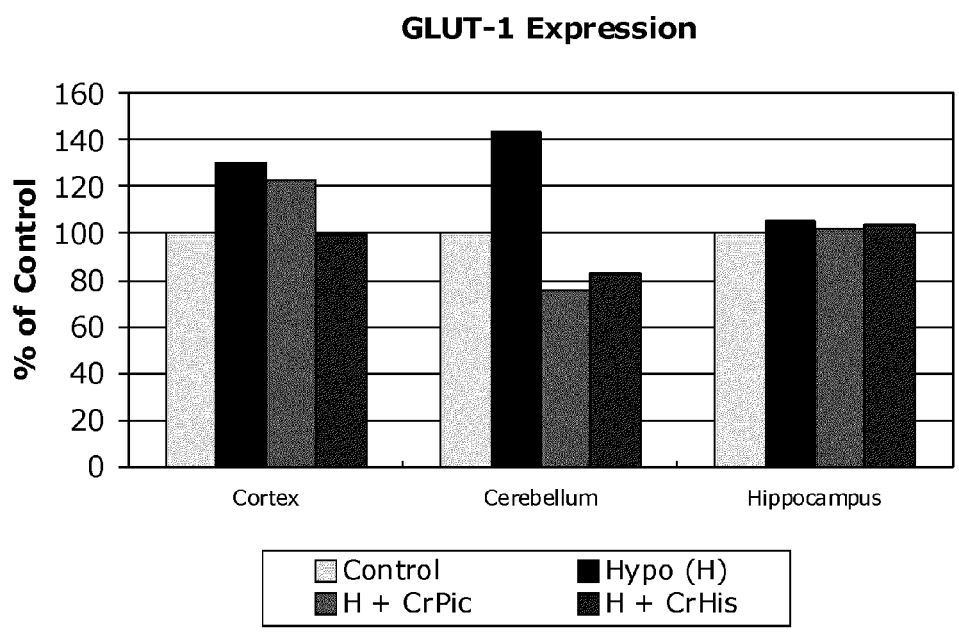
FIG. 3 is a bar graph showing GLUT-1 transporter levels after treatment for control (no treatment) and treatment groups (H, H+CrPic, and H+CrHis), as described in Example 1.

As shown in FIG. 3, hypoglycemia significantly raised brain GLUT-1 transporter levels. The hypoglycemia-induced GLUT-1 increase was reduced in animals that received chromium treatment. These data suggest that chromium may play a protective role by regulating GLUT-1 levels in order that excessive glucose does not enter the cells, which may lead to cell damage.

Figure 4:
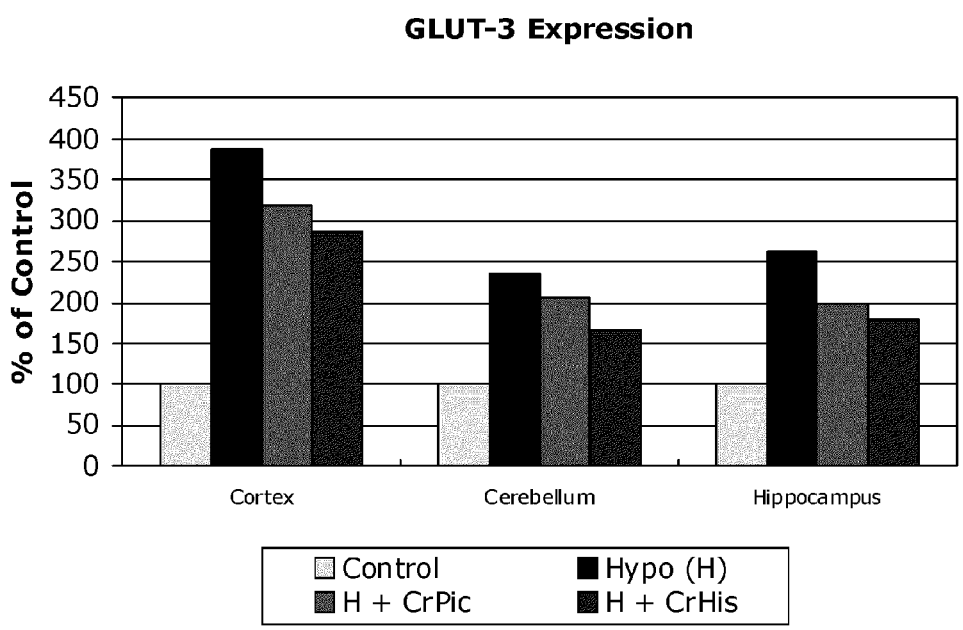
FIG. 4 is a bar graph showing GLUT-3 transporter levels after treatment for control (no treatment) and treatment groups (H, H+CrPic, and H+CrHis), as described in Example 1.

As shown in FIG. 4, hypoglycemia significantly raised brain GLUT-3 transporter levels. The hypoglycemia-induced GLUT-3 increase was reduced in animals that received chromium treatment. These data suggest that chromium may play a protective role by regulating GLUT-3 levels in order that excessive glucose does not enter the cells, which may lead to cell damage.

Figure 5:
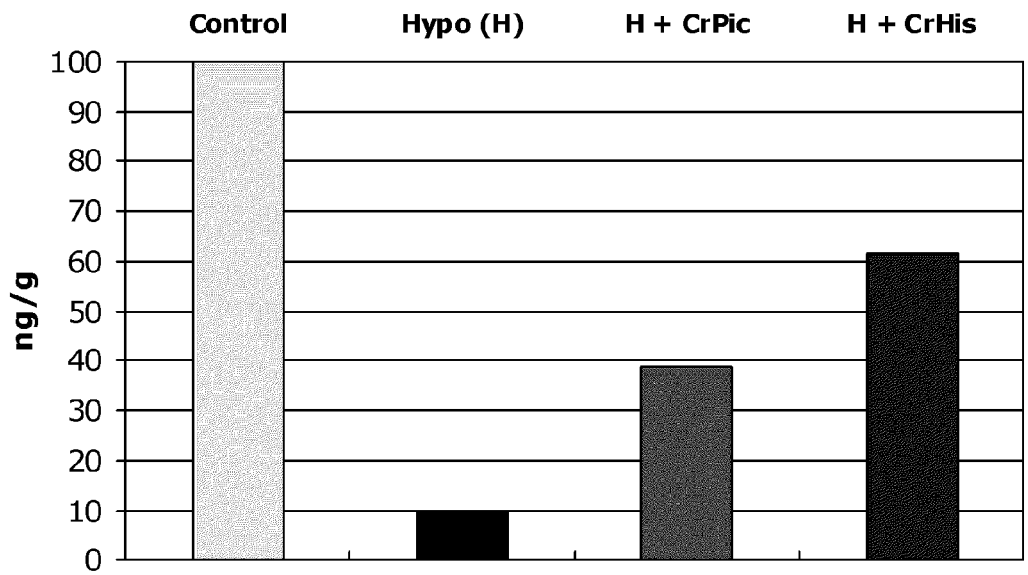
FIG. 5 is a bar graph showing hippocampus Nrf2 (nuclear factor erythroid 2 related factor 2) levels after treatment for control (no treatment) and treatment groups (H, H+CrPic, and H+CrHis), as described in Example 1.

As shown in FIG. 5, hypoglycemia significantly lowered brain Nrf2 tissue levels (cytoprotective protein). The hypoglycemia-induced Nrf2 decrease was reduced by chromium treatment. As reduced Nrf2 levels have been implicated in cognitive impairment, these data demonstrate the usefulness of chromium in protecting against hypoglycemia-related conditions and disorders, including cognitive dysfunction.

Figure 6:
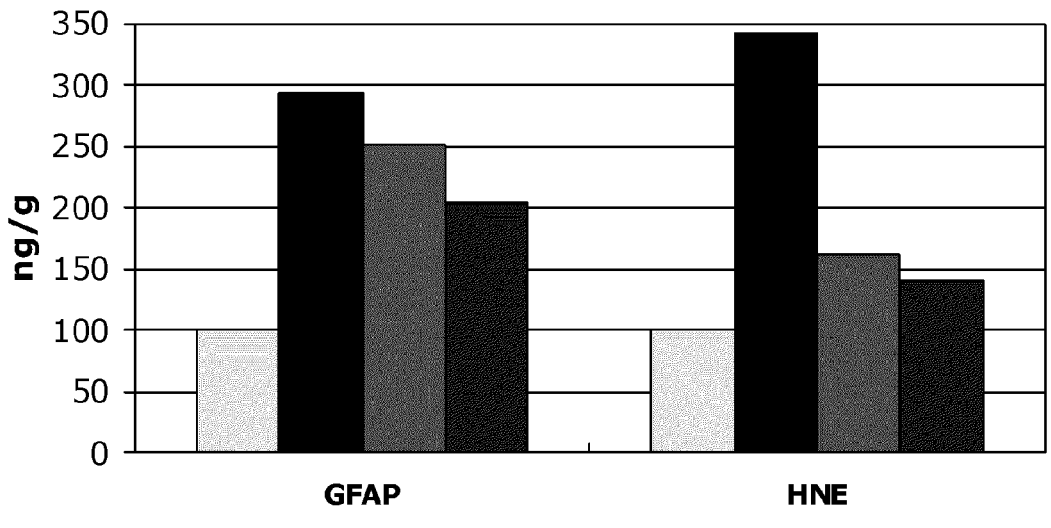
FIG. 6 is a bar graph showing hippocampus GFAP (glial fibrillary acidic protein) & HNE (4-Hydroxynonenal) levels after treatment for control (no treatment) and treatment groups (H, H+CrPic, and H+CrHis), as described in Example 1.

As shown in FIG. 6, hypoglycemia significantly raised brain GFAP and HNE tissue levels (markers of neuronal and oxidative damage). GFAP and HNE levels were lowered by chromium treatment. These data demonstrate the usefulness of chromium in protecting against hypoglycemia-related conditions, including neuronal damage.

TABLE 1

Comparison of Hypoglycemic Brain Damage Markers (mean ± s.d.)

| | Control | Hypo | CrPic | CrHis |
|---|---|---|---|---|
| Serum Glucose at 0.5 hrs (mg/dL) | 115.6 ± 5.5 | 42.6 ± 6.5 | 40.7 ± 5.2 | 42.6 ± 6.8 |
| Brain Cr Levels (ng/g) | 18.5 ± 2.0 | 15.3 ± 1.7 | 20.3 ± 1.8 | 21.6 ± 1.7 |
| Cortex GLUT-1 Expression (% Control) | 100 ± 3.3 | 130.4 ± 9.3 | 122.8 ± 1.3 | 99.9 ± 7.3 |
| Cerebellum GLUT-1 Expression (% Control) | 100 ± 4.7 | 143.3 ± 8.0 | 75.6 ± 7.6 | 83.0 ± 4.2 |
| Hippocampus GLUT-1 Expression (% Control) | 100 ± 6.3 | 105.3 ± 5.3 | 102.3 ± 5.5 | 103.7 ± 2.8 |
| Cortex GLUT-3 Expression (% Control) | 100 ± 8.0 | 387.9 ± 20.9 | 319.5 ± 14.6 | 287.5 ± 31.3 |
| Cerebellum GLUT-3 Expression (% Control) | 100 ± 7.3 | 235.7 ± 1.1 | 206.3 ± 6.4 | 166.9 ± 2.2 |
| Hippocampus GLUT-3 Expression (% Control) | 100 ± 15.1 | 261.2 ± 3.0 | 198.6 ± 8.9 | 177.8 ± 4.7 |

TABLE 1-continued

Comparison of Hypoglycemic Brain Damage Markers (mean ± s.d.)

|  | Control | Hypo | CrPic | CrHis |
|---|---|---|---|---|
| Hippocampus Nrf2 Expression (% Control) | 100 ± 5.9 | 18.0 ± 2.9 | 38.9 ± 3.6 | 61.8 ± 1.4 |
| Hippocampus GFAP Expression (% Control) | 100 ± 7.4 | 294.1 ± 7.0 | 251.2 ± 9.1 | 204.9 ± 4.9 |
| Hippocampus HNE Expression (% Control) | 100 ± 18.0 | 342.2 ± 14.2 | 162.5 ± 12.4 | 140.1 ± 12.0 |

The data above demonstrate that chromium pre-treatment can significantly alleviate the negative side effects caused by hypoglycemia.

Example 2

Chromium and Insulin can form a Chromium-Insulin Complex

In order to evaluate chromium's potential to form a complex with insulin molecules the following was performed.

100 μl of insulin (10 mg/ml) was mixed with 200 μl of chromium histidinate ("Cr-His") (26 mg/ml) at room temperature (20° C.) which formed a white precipitate. The precipitate was collected by centrifugation and washed once with deionized water. The precipitate was then redissolved in 25 mM potassium phosphate buffer pH 7.4. The original supernatant and redissolved precipitate were then run through a size-exclusion column (for example, a 3 μM 100 Å column available from Agilent Bio having a resolving range of 100-100,000 Da; larger molecules eluting first) and analyzed with UV-Vis and ICPMS analysis.

Figure 14:
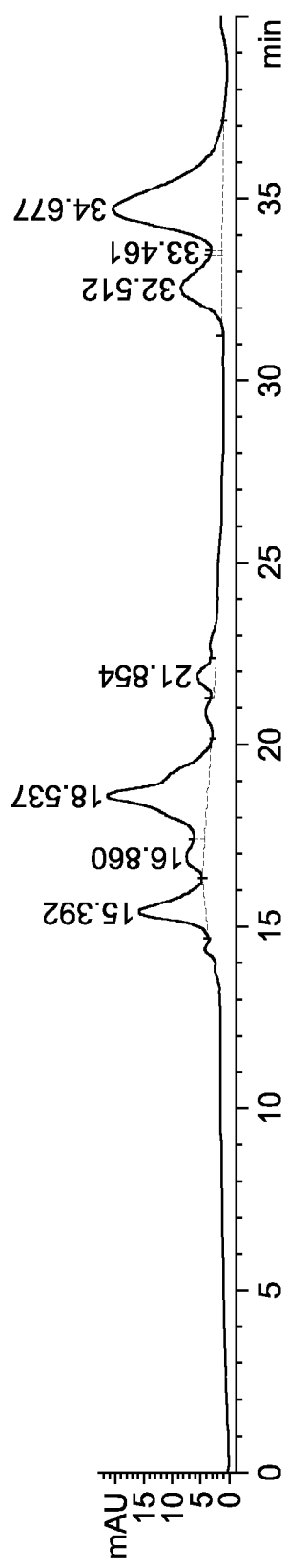
FIG. 14 is a graph showing UV absorbance (mAU) over time of chromium histidinate eluted through a sizing column.
Figure 15:
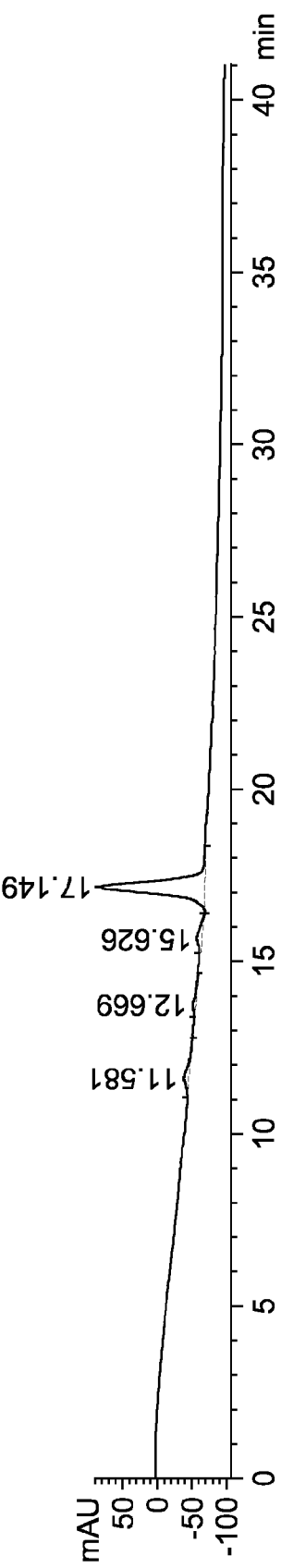
FIG. 15 is a graph showing UV absorbance (mAU) over time of insulin eluted through a sizing column.

Cr-His and insulin controls (i.e. same concentrations as in the Cr-His and insulin mixture) were run through the column. FIG. 14 shows the UV 280 nm plot of chromium histidinate alone while FIG. 15 shows the UV 214 nm plot of insulin alone.

Figure 16:
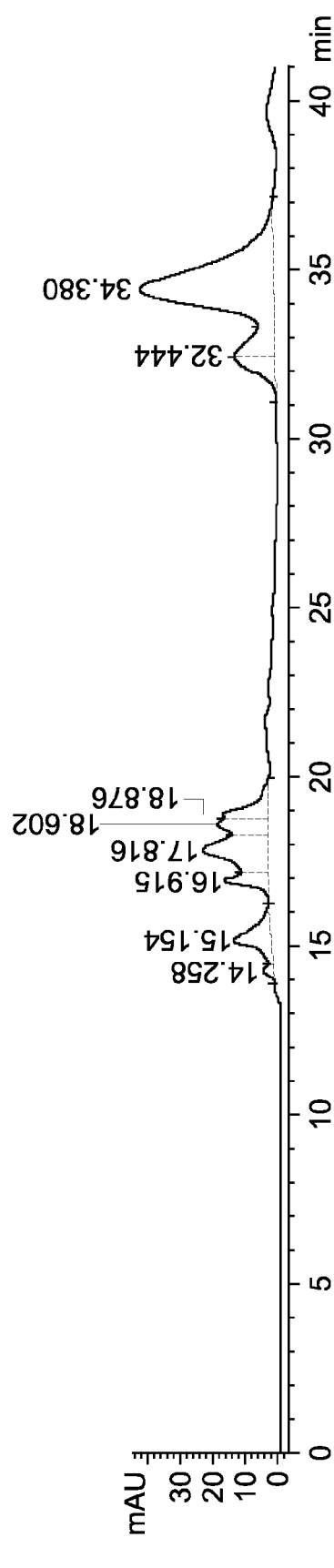
FIG. 16 is a graph showing UV absorbance (mAU) over time of supernatant from a chromium insulin composition eluted through a sizing column.
Figure 17:
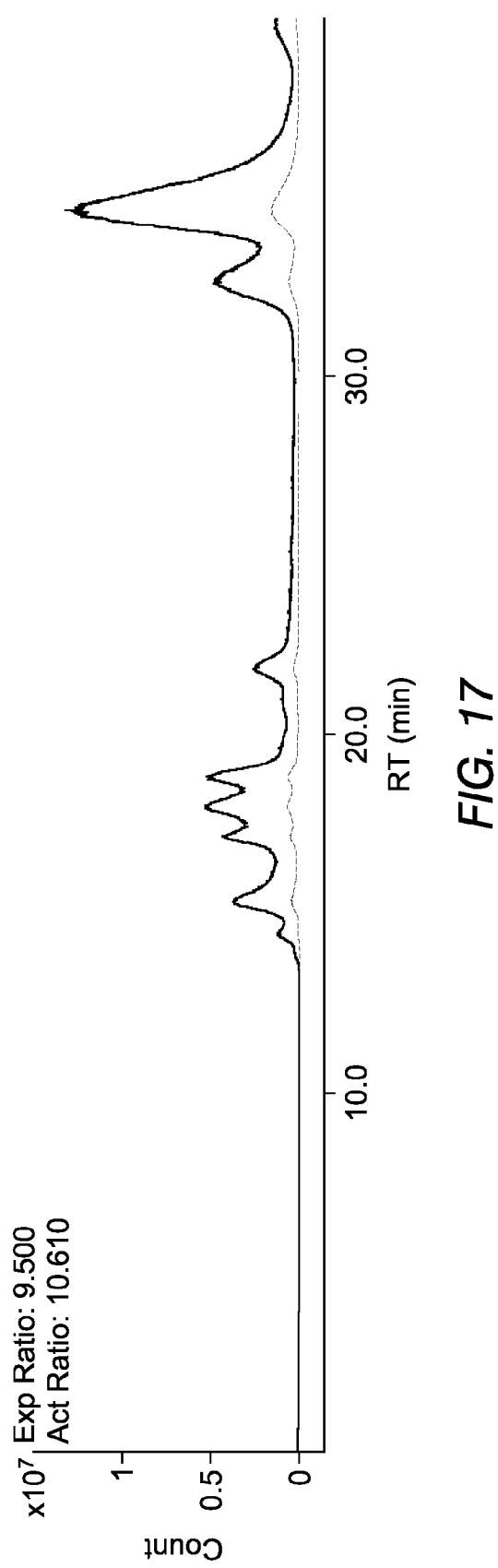
FIG. 17 is a graph showing counts over time output from an inductively coupled plasma mass spectrometry ("ICPMS") device targeting $^{52}Cr$ of supernatant from a chromium insulin composition eluted through a sizing column.

FIG. 16 shows the UV 280 nm plot of the supernatant and FIG. 17 shows the ICPMS plot targeting $^{52}$Cr. Thus, in comparison to the Cr-His control, the analysis of the supernatant indicated that much Cr-His remained in the supernatant.

Figure 18:
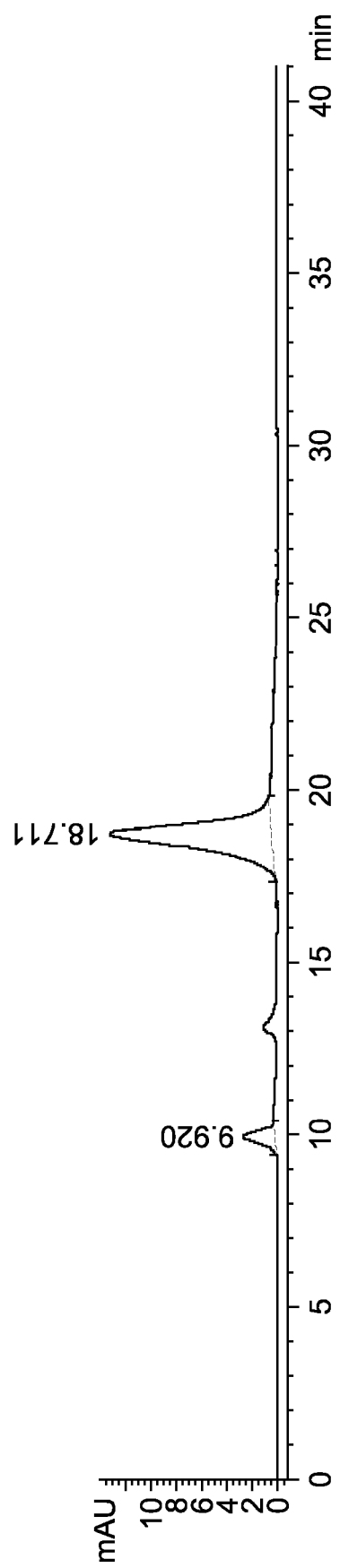
FIG. 18 is a graph showing UV absorbance (mAU) over time of a redissolved precipitate from a chromium insulin composition eluted through a sizing column indicating the existence of a chromium-insulin complex.
Figure 19:
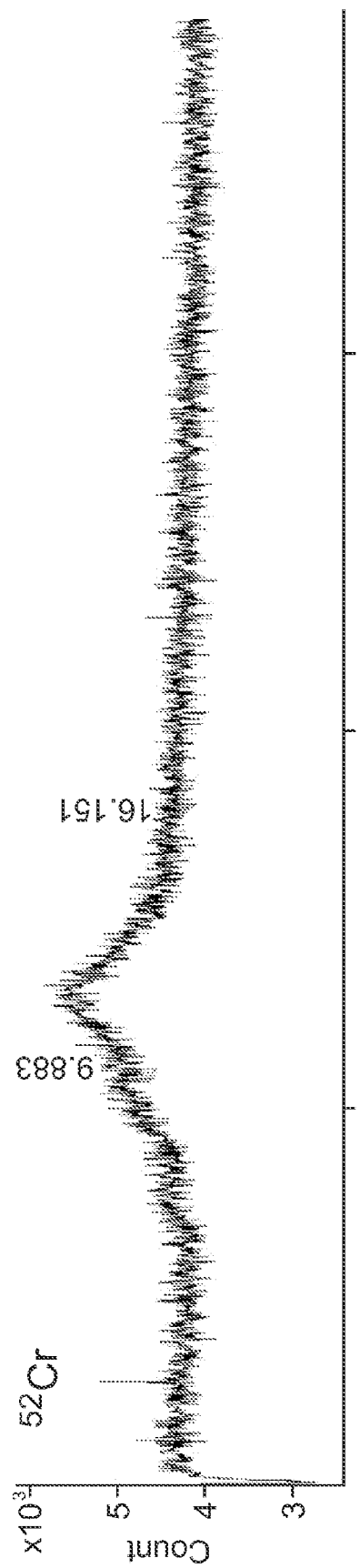
FIG. 19 is a graph showing counts over time from output from an ICPMS device targeting $^{52}Cr$ of a redissolved precipitate from a chromium insulin composition eluted through a sizing column indicating the existence of a chromium-insulin complex.
Figure 20:
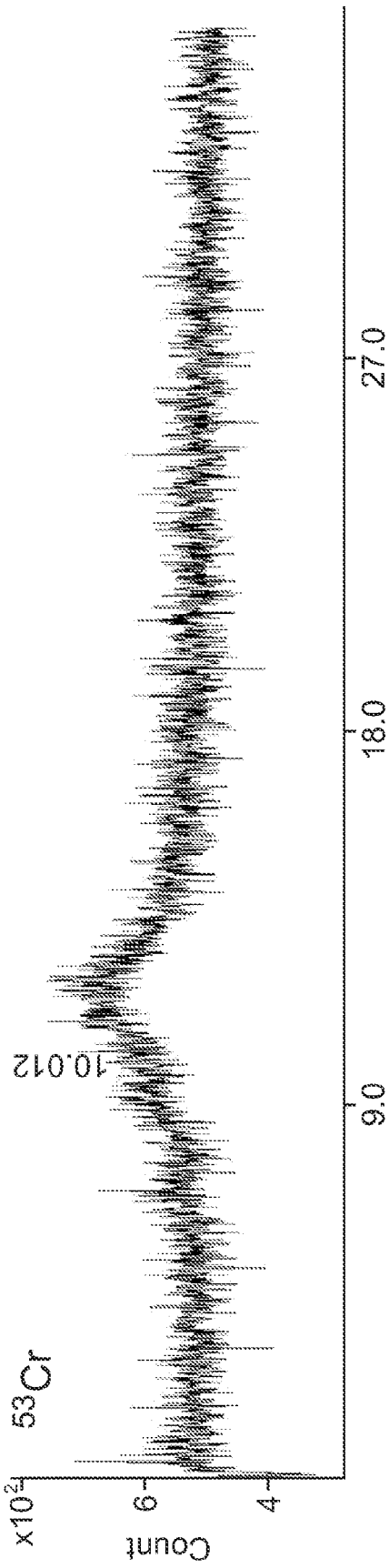
FIG. 20 is a graph showing counts over time from output from an ICPMS device targeting $^{53}$Cr of a redissolved precipitate from a chromium insulin composition eluted through a sizing column indicating the existence of a chromium-insulin complex.

FIG. 18 shows the UV 214 nm plot for the redissolved precipitate. As shown, a peak at about ten minutes was detected. FIG. 19 shows the ICPMS plot targeting $^{52}$Cr and FIG. 20 shows the ICPMS plot targeting $^{53}$Cr for the redissolved precipitate. Again a peak around ten minutes indicated the presence of chromium. The molecular weight of this elution at around ten minutes was estimated at about 36 kDa. These data strongly suggest that chromium forms a complex with insulin.

Example 3

Chromium-Insulin Compositions Raise Serum Insulin Levels and Reduce Serum Glucose Levels in Normal Mice to a Greater Extent than Insulin or Zinc-Insulin Compositions In order to evaluate the effect of chromium-insulin compositions on serum insulin levels and serum glucose levels in normal mice, the following was performed.

C57BL/6 mice (five mice per study group) were injected with 0.5 U/kg of body weight i.p. of insulin in three different forms: insulin alone, zinc-insulin, and chromium-insulin. Serum insulin levels were measured over time. The serum insulin levels were determined by rat insulin enzyme-linked immunosorbent assay (ELISA) kit from Crystal Chem (Downers Grove, Ill.).

Figure 21:
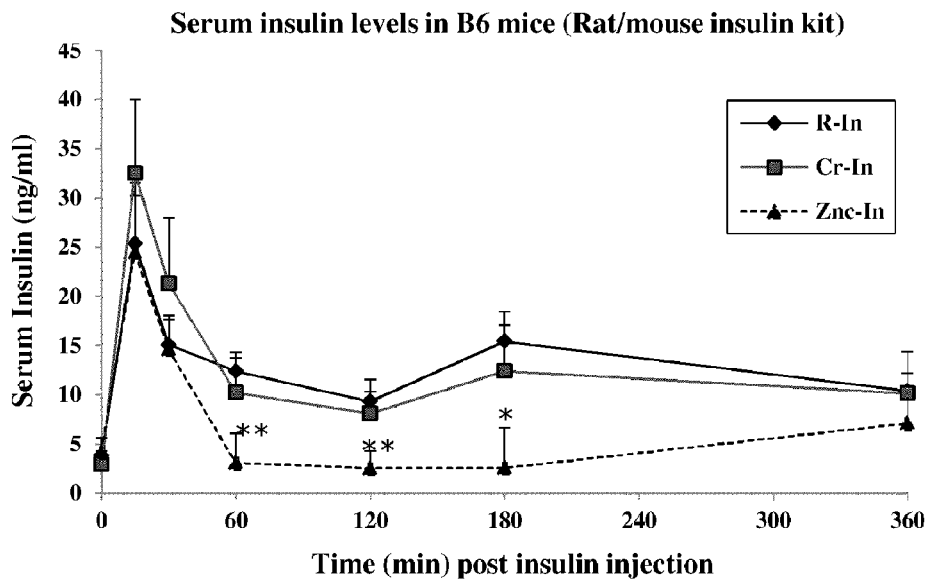
FIG. 21 is a line graph showing serum insulin levels over time for mice treated with either regular insulin (R—In), chromium insulin (Cr—In), or zinc-insulin (Znc-In).

FIG. 21 shows the results. As shown in FIG. 21, the same amount of insulin provided in the form of a chromium-insulin composition had a different, beneficial pharmacokinetic profile than the same amount of insulin provided as insulin alone and zinc insulin compositions. Of note, the early time points indicate that chromium insulin injections raised serum insulin higher than the other compositions. Serum insulin levels remained higher for chromium insulin in the early time period. As such, the data show that the compositions provided herein provide improved absorption of insulin.

Figure 22:
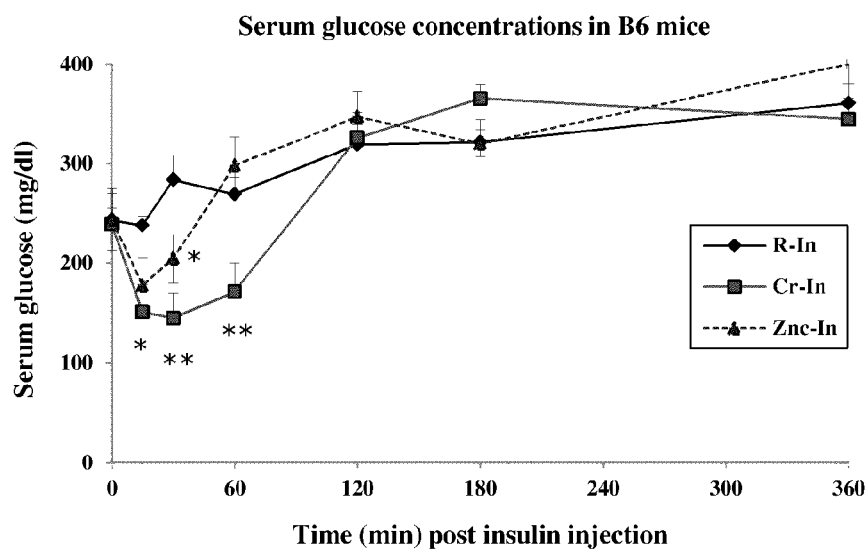
FIG. 22 is a line graph showing serum glucose levels over time for mice treated with either regular insulin (R—In), chromium insulin (Cr—In), or zinc-insulin (Znc-In).

In order to determine if the improved absorption data correlated with improved therapeutic effects, serum glucose levels were measured over time using the FreeStyle blood glucose monitoring system (TheraSense, Phoenix, Ariz.). The data are shown in FIG. 22. shows that insulin provided as a chromium insulin composition lowered serum glucose levels to a greater degree than the same amount of insulin provided as insulin alone, or a zinc-insulin composition. These data demonstrate the improved therapeutic efficacy of insulin, when provided in a composition comprising chromium.

Example 4

Chromium-Insulin Compositions Raise Serum Insulin Levels and Reduce Serum Glucose Levels in Diabetic Mice Faster than Insulin Alone and Faster than Zinc-Insulin Compositions In order to evaluate the effect of chromium-insulin compositions on serum insulin levels and serum glucose levels in diabetic mice, the following was performed.

KKAy mice (5 mice per study group) were injected with 0.5 U/kg of body weight i.p. of insulin in three different forms: insulin alone, zinc-insulin, and chromium-insulin. Serum insulin levels were measured over time.

Serum insulin levels were measured over time. The serum insulin levels were determined by rat insulin enzyme-linked immunosorbent assay (ELISA) kit from Crystal Chem (Downers Grove, Ill.).

Figure 23:
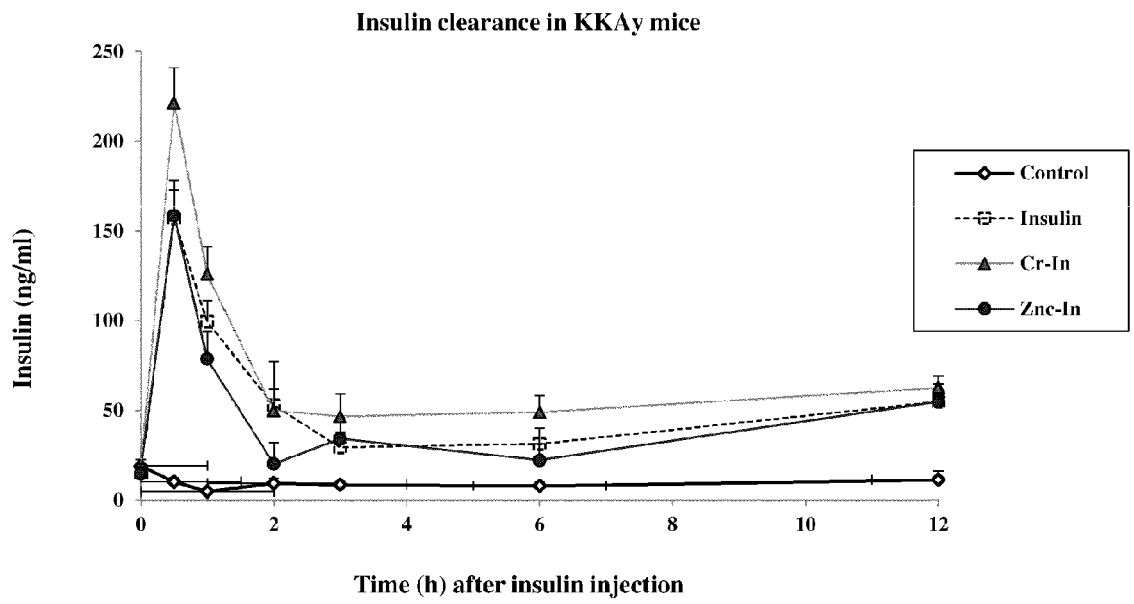
FIG. 23 is a line graph showing serum insulin levels over time for diabetic mice treated with either saline (Control), regular insulin (Insulin), chromium insulin (Cr—In), or zinc-insulin (Znc-In).

FIG. 23 shows the results. As shown in FIG. 23, chromium-insulin had a different pharmacokinetic profile than both insulin alone and zinc-insulin. Of note, the early time points indicate that chromium insulin injections raised serum insulin higher than the other compositions. Serum insulin levels remained higher in animals receiving insulin in the form of a chromium insulin composition in the early time period. These data confirm the observed increase in absorption of insulin, when provided as a chromium insulin composition.

Figure 24:
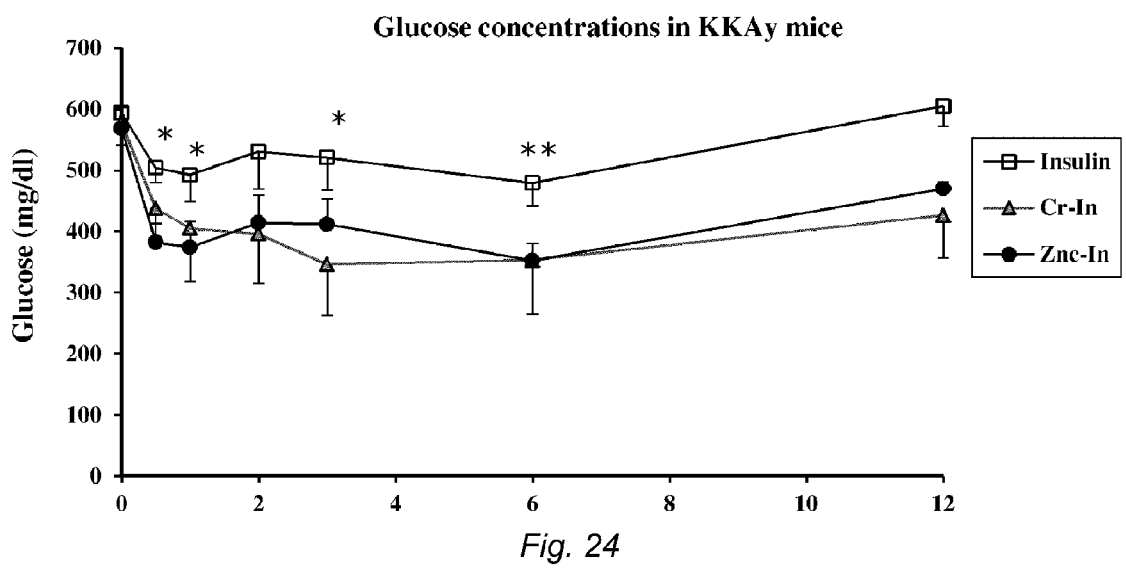
FIG. 24 is a line graph showing serum glucose levels over time for diabetic mice treated with either regular insulin (Insulin), chromium insulin (Cr—In), or zinc-insulin (Znc-In).

FIG. 24 shows the serum glucose levels measured over time as determined using the FreeStyle blood glucose monitoring system (TheraSense, Phoenix, Ariz.). As shown in FIG. 24, chromium insulin injections lowered serum glucose levels below insulin alone.

Example 5

Chromium-Insulin Compositions Lower Glucose Levels to a Greater Extent than Zinc-Insulin Compositions In order to evaluate the effect of chromium-insulin compositions in comparison to zinc-insulin compositions in a diabetic rat model, the following was performed.

Four experimental groups, each containing seven Wistar rats were formed as follows:
1) Control: injected with saline;
2) Type 1: injected with 65 mg/kg i.p. of streptozotocin ("STZ") (to model type 1 diabetes);
3) +ZnIns: injected with 65 mg/kg i.p. of STZ and injected with 6.23 mcg of ZnO and 3 IU of insulin per 100 g of body weight;
4) +CrIns: injected with 65 mg/kg i.p. of STZ and injected with 47.7 mcg Cr-His and 3 IU of insulin per 100 g of body weight.

Figure 25:
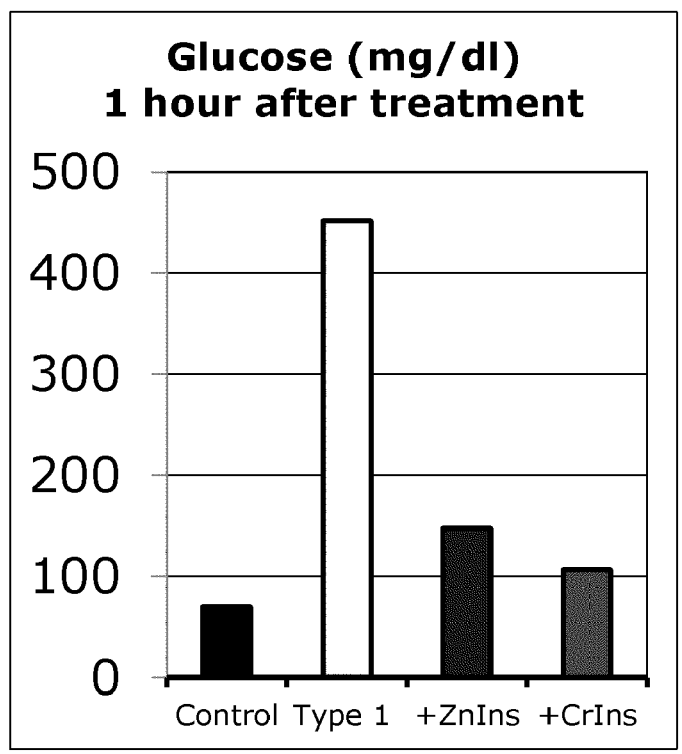
FIG. 25 is a bar graph showing serum glucose levels after treatment for control and treatment groups (Control, Type 1, +ZnIns, +CrIns), as described in Example 5.

Serum Glucose levels were calculated using Glucose Oxidase Peroxidase methods (GOD/POD Kits) one hour after treatment. FIG. 25 shows the results in graphical form. As shown in FIG. 25, the +CrIns had lower serum glucose levels than the +ZnIns group. These data confirm that insulin, when provided as a chromium insulin composition, exhibits unexpected and favorable therapeutic effects in terms of lowering serum glucose levels, when compared to insulin alone, or compositions comprising zinc and insulin.

Example 6

Chromium-Insulin Compositions Maintain Normal Body Weight to a Greater Extent than Zinc-Insulin Compositions in Diabetic Rats In order to evaluate the effect of chromium-insulin compositions in comparison to zinc-insulin compositions in a diabetic rat model, the following was performed.

Four experimental groups, each containing seven Wistar rats were formed as follows:
1) Control: injected with saline;
2) Type 1: injected with 40 mg/kg i.p. of STZ;
3) +ZnIns: injected with 40 mg/kg i.p. of STZ and injected with 0.5 IU of zinc-insulin;
4) +CrIns: injected with 40 mg/kg i.p. of STZ and injected with 0.8 IU.

The rats were injected daily for eight weeks. The rats initial average and final average body weights are shown below in Table 2.

TABLE 2

Effect of Insulin-chelate Type on Body Weight in Type 1 Induced Rats
Effect of insulin-chelate type on body weight of type-1 diabetes induced rats (n = 7 per group)

| Groups[1] | Response variables[2] | | |
|---|---|---|---|
| | Initial BW, g | Final BW, g | BW Change, % |
| Control | 195.57 ± 4.97 | 253.00 ± 11.93[a] | +30.13 ± 8.04[a] |
| STZ | 195.86 ± 5.23 | 166.29 ± 10.33[c] | −14.62 ± 5.96[c] |
| STZ + Zn-Insulin | 195.43 ± 4.35 | 183.83 ± 7.96[bc] | −4.77 ± 3.92[b] |
| STZ + Cr-Insulin | 195.71 ± 4.90 | 195.57 ± 3.83[b] | +0.25 ± 2.97[b] |
| | p < 1.00 | 0.0001 | 0.0001 |

The data above demonstrate that treatment with insulin provided as a chromium insulin composition can significantly alleviate the negative side effects, such as weight loss, caused by hypoglycemia. The beneficial effect of the chromium insulin complexes was significantly greater than that observed with a composition comprising zinc and insulin.

Example 7

Composition Comprising Chromium and Insulin Having Synergistic Effect in Treating Diabetes A first, second, third, and fourth subject having similar weight, age, insulin sensitivity, and other characteristics are identified as having diabetes. The subjects each present one or more symptoms associated with diabetes, such as a fasting serum glucose level over 126 mg/dL.

The first subject is parenterally administered a control saline solution.

The second subject is parenterally administered a dosage X of chromium between 25 and 2,000 µg.

The third subject is parenterally administered a dosage Y of insulin between 1 unit and 500 units.

The fourth subject is parenterally administered a composition comprising the dosage X of chromium between 25 and 2,000 µg and dosage Y of insulin between 1 unit and 500 units.

The subjects' fasting serum glucose levels are measured before and after administration of the chromium. After administration of the chromium, the first subject is observed to no change in serum glucose level. The second subject is observed to have a reduced serum glucose level. The third subject is observed to have a reduced glucose level that is lower than that for the third subject, and has become hypoglycemic. The fourth subject is observed to have a reduced serum glucose level lower than that of the first and second subject, but higher than that of the third subject, and not hypoglycemic.

Example 8

In order to evaluate the efficacy of a parenterally administered composition comprising chromium and insulin, diabetic animals were parenterally administered a composition comprising chromium and insulin, and indicators of metabolic function, diabetic profile, and markers of hypoglycemic brain damage were compared in animals with and without administration of chromium. In addition, the administration of chromium was compared to the administration of zinc.

Forty-two Wistar rats were assigned to one of 6 experimental groups: 1) positive control: rats injected with saline 2) type-1 diabetes group: rats injected with streptozotocin (STZ, 65 mg/kg i.p.) to damage beta cells (n=35). Diabetic rats were then administered with a) none, b) Zn alone (6.23 µg ZnO), c) Cr alone (47.7 µg Cr-histidinate), d) Zn-insulin (6.23 µg ZnO+3 IU Ins/100 g BW), or e) Cr-insulin (47.7 µg Cr-histidinate+3 IU Ins/100 g BW), daily for 26 days (n=7 per subgroup). Body weights were measured at the beginning and end of the experiment.

Blood samples were collected on days—2 (beginning), 0 (induction), 4, 6, 12, and 26 for blood biochemistry. At the end of the experiment, rats were sacrificed for brain tissue GLUTs (1 and 3). Data were analyzed using one-way ANOVA with LSD option for mean comparison. Body weight at the beginning of the experiment was not different across the groups. However, diabetic rats at the end of the experiment lost body weight as compared to the control rats. Diabetic rats treated with Zn-Ins and Cr-Ins lost less body weight than untreated diabetic rats. Diabetes induction was associated with decreased serum insulin and total protein, and CK (creatinine kinase) levels and increased serum glucose, urea, creatinine, and K levels as well as AST (aspartate aminotransferase), ALT (alanine aminotransferase), ALP (alkaline phosphatase) and LDH (lactate dehydrogenase) activities.

Efficacy of CrIns to restore metabolic profile was equivalent or superior to ZnIns. During the experiment, injecting CrIns was more effective to reduce elevated serum glucose level than injecting ZnIns. Brain GLUTs expressions were depressed by diabetes induction. CrIns treatment was superior to other treatment choices in terms of alleviating cerebral GLUTs expressions. In conclusion, it appears that CrIns is superior to ZnIns to suppress hyperglycemia through dual effect of Cr and exogenous insulin, probably resulting from potentiated insulin action and internalized glucose.

The results of the study are shown in Tables 2-7 and FIGS. 7-13.

TABLE 3

Effect of insulin-chelate type on body weight of type-1 diabetes induced rats (n = 7 per group).

| Groups[1] | Response variables[2] | | |
|---|---|---|---|
| | Initial BW, g | Final BW, g | BW Change, % |
| Control | 195.57 ± 4.97 | 253.00 ± 11.93[a] | +30.13 ± 8.04[a] |
| STZ | 195.86 ± 5.23 | 166.29 ± 10.33[c] | −14.62 ± 5.96[c] |
| STZ + Zn | 195.43 ± 7.63 | 175.71 ± 7.67[bc] | −9.71 ± 4.03[bc] |
| STZ + Cr | 195.43 ± 5.94 | 176.57 ± 12.27[bc] | −10.17 ± 3.94[bc] |
| STZ + Zn-Insulin | 195.43 ± 4.35 | 183.83 ± 7.96[bc] | −4.77 ± 3.92[b] |
| STZ + Cr-Insulin | 195.71 ± 4.90 | 195.57 ± 3.83[b] | +0.25 ± 2.97[b] |
| | p < | | |
| | 1.00 | 0.0001 | 0.0001 |

[1]Rats in control group was injected with saline. STZ = streptozotocin (STZ, 40 mg/kg i.p.); STZ + Zn-Insulin = STZ + Zn-insulin (0.5 IU); STZ + Cr-Insulin = STZ + Cr-insulin (0.8 IU) daily for 26 days.
[2]Different superscripts within columns differ ($p < 0.05$).

As shown in Table 2, compared to all other treatment groups including ZnIns, CrIns resulted in the lowest reduction in body weight. These data suggest that CrIns is superior to ZnIns in treating diabetes.

TABLE 4

Effect of insulin-chelate type on glucose pattern of type-1 diabetes induced rats.

| Response variables[3] | Groups[1,2] | | | | | |
|---|---|---|---|---|---|---|
| | Control | STZ | STZ + Zn | STZ + Cr | STZ + Zn-Insulin | STZ + Cr-Insulin |
| Basal level | | | 95 ± 1.59 | | | |
| After STZ administration | | | 324 ± 15.4 | | | |
| Day 4 | | | | | | |
| Before | 60 | 473 | 457 | 403 | 374 | 462 |
| After | 69 | 439 | 303 | 237 | 118 | 94 |
| 6 | | | | | | |
| Before | 77 | 392 | 350 | 330 | 388 | 371 |
| After | 71 | 441 | 372 | 349 | 120 | 95 |
| 12 | | | | | | |
| Before | 70 | 451 | 421 | 340 | 400 | 372 |
| After | 70 | 446 | 412 | 349 | 138 | 104 |
| 21 | | | | | | |
| Before | 61 | 438 | 380 | 368 | 419 | 376 |
| After | 70 | 452 | 329 | 303 | 148 | 107 |
| Pooled SEM | | | 25.33 | | | |
| ANOVA | | | | | | |
| Group | | | 0.0001 | | | |
| Time relative to injection | | | 0.0001 | | | |
| Group × time relative to injection | | | 0.0001 | | | |
| Day | | | 0.36 | | | |
| Group × day | | | 0.50 | | | |
| Time relative to injection × day | | | 0.0003 | | | |

TABLE 4-continued

Effect of insulin-chelate type on glucose pattern of type-1 diabetes induced rats.

| Response variables[3] | Groups[1,2] | | | | | |
|---|---|---|---|---|---|---|
| | Control | STZ | STZ + Zn | STZ + Cr | STZ + Zn-Insulin | STZ + Cr-Insulin |
| Group × time relative to injection × day | | | 0.19 | | | |

[1]Rats in control group was injected with saline. STZ = streptozotocin (STZ, 40 mg/kg i.p.); STZ + Zn-Insulin = STZ + Zn-insulin (0.5 IU); STZ + Cr-Insulin = STZ + Cr-insulin (0.8 IU) daily for 26 days.
[2]Different superscripts within rows differ (p < 0.05).

TABLE 5

Effect of insulin-chelate type on blood biochemistry of type-1 diabetes induced rats at the end of the animal experimentation

| Response variables[3] | Groups[1,2] | | | | | | p |
|---|---|---|---|---|---|---|---|
| | Control | STZ | STZ + Zn | STZ + Cr | STZ + Zn-Insulin | STZ + Cr-Insulin | |
| Insulin, µU/mL | 36.0 ± 1.4[a] | 19.4 ± 1.5[c] | 20.9 ± 0.9[bc] | 22.0 ± 0.8[bc] | 23.0 ± 1.1[b] | 23.9 ± 1.1[b] | 0.0001 |
| Glucose, mg/dL | 128 ± 7[e] | 478 ± 20[a] | 456 ± 13[ab] | 423 ± 15[bc] | 416 ± 10[cd] | 379 ± 6[d] | 0.0001 |
| AST, U/L | 141 ± 8[c] | 343 ± 17[a] | 328 ± 17[a] | 291 ± 24[ab] | 288 ± 30[ab] | 268 ± 16[b] | 0.0001 |
| ALT, U/L | 87 ± 6[d] | 220 ± 11[a] | 143 ± 9[b] | 125 ± 12[bc] | 115 ± 9[c] | 102 ± 3[cd] | 0.0001 |
| ALP, U/L | 133 ± 5[d] | 550 ± 13[a] | 453 ± 11[b] | 442 ± 13[bc] | 429 ± 17[bc] | 411 ± 8[c] | 0.0001 |
| LDH, U/L | 1465 ± 146[c] | 2716 ± 99[a] | 2564 ± 85[ab] | 2367 ± 52[b] | 2523 ± 78[ab] | 2329 ± 83[b] | 0.0001 |
| CK, U/L | 15958 ± 3256[a] | 6188 ± 1166[b] | 6872 ± 1248[b] | 6745 ± 934[b] | 7989 ± 523[b] | 8352 ± 338[b] | 0.001 |
| Total protein, g/dL | 6.77 ± 0.18[a] | 6.01 ± 0.24[b] | 5.91 ± 0.07[b] | 6.07 ± 0.12[b] | 6.33 ± 0.17[ab] | 6.67 ± 0.19[a] | 0.002 |
| Albumin, g/dL | 2.86 ± 0.08[a] | 2.77 ± 0.10[ab] | 2.59 ± 0.06[b] | 2.74 ± 0.06[ab] | 2.67 ± 0.08[ab] | 2.84 ± 0.06[a] | 0.09 |
| Urea, mg/dL | 31.1 ± 1.4[d] | 83.6 ± 3.9[a] | 65.6 ± 1.0[b] | 62.1 ± 2.5[bc] | 61.3 ± 2.9[bc] | 57.9 ± 2.1[c] | 0.0001 |
| Creatinine, mg/dL | 0.55 ± 0.02[d] | 1.60 ± 0.08[a] | 1.05 ± 0.07[b] | 0.90 ± 0.08[bc] | 0.85 ± 0.14[bc] | 0.78 ± 0.09[cd] | 0.0001 |
| Uric acid, mg/dL | 4.23 ± 0.29[c] | 7.67 ± 0.34[a] | 6.49 ± 0.69[ab] | 6.21 ± 0.57[b] | 5.75 ± 0.33[b] | 5.59 ± 0.16[b] | 0.0002 |
| K, mmol/L | 4.65 ± 0.10[c] | 5.98 ± 0.20[a] | 5.53 ± 0.09[b] | 5.57 ± 0.12[b] | 5.48 ± 0.08[b] | 5.29 ± 0.15[b] | 0.0001 |

[1]Rats in control group was injected with saline. STZ = streptozotocin (STZ, 40 mg/kg i.p.); STZ + Zn-Insulin = STZ + Zn-insulin (0.5 IU); STZ + Cr-Insulin = STZ + Cr-insulin (0.8 IU) daily for 26 days.
[2]Different superscripts within rows differ (p < 0.05).
[3]AST = aspartate aminotransferase; ALT = alanine aminotransferase; ALP = alkaline phosphatase; LDH = lactate dehydrogenase; CK = creatinine kinase As shown in Table 4, compared to all other treatment groups including ZnIns, CrIns was most effective at returning levels of serum insulin, CK, total protein, albumin, serum glucose, AST, ALT, ALP, LDH, urea, creatinine, and uric acid to control levels.

TABLE 6

Effect of insulin-chelate type on cerebral glucose transporter (GLUT) expressions in type-1 diabetes induced rats.

| Group[1] | Response variables[2] | |
|---|---|---|
| | GLUT-1 | GLUT-3 |
| Control | 100.00 ± 3.50[a] | 100.00 ± 4.33[a] |
| STZ | 31.94 ± 1.42[d] | 25.56 ± 3.00[d] |
| STZ + Zn | 46.82 ± 3.23[c] | 43.41 ± 3.53[c] |
| STZ + Cr | 53.81 ± 3.53[c] | 49.41 ± 2.39[c] |
| STZ + Zn-Insulin | 75.47 ± 3.94[b] | 81.54 ± 5.80[b] |
| STZ + Cr-Insulin | 89.71 ± 4.62[a] | 95.60 ± 3.52[a] |
| | p < 0.0001 | 0.0001 |

[1]Rats in control group was injected with saline. STZ = streptozotocin (STZ, 40 mg/kg i.p.); STZ + Zn-Insulin = STZ + Zn-insulin (0.5 IU); STZ + Cr-Insulin = STZ + Cr-insulin (0.8 IU) daily for 26 days.
[2]Different superscripts within columns differ (p < 0.05).

As shown in Table 5, compared to all other treatment groups including ZnIns, CrIns resulted in the highest levels of GLUT-1 and GLUT-3 expression. These data suggest that CrIns is superior to ZnIns to suppress hyperglycemia and treat diabetes.

TABLE 7

Effect of insulin-chelate type on serum and brain chemicals (n = 7 per group).

| Groups[1] | Response variables[2] | | | |
|---|---|---|---|---|
| | Serum Cr (mcg/g) | Brain Cr (ng/g) | Brain Serotonin (mcg/g) | Brain Tryptophan (mcg/g) |
| Control | 75.17 ± 2.54[a] | 24.77 ± 1.52[a] | 640 ± 4[a] | 9.19 ± 0.43[a] |
| STZ | 33.38 ± 2.86[d] | 8.81 ± 0.70[d] | 484 ± 5[e] | 4.01 ± 0.23[d] |
| STZ + Zn | 33.65 ± 2.26[d] | 9.05 ± 0.56[d] | 492 ± 5[e] | 4.54 ± 0.23[d] |
| STZ + Cr | 48.64 ± 2.70[c] | 11.87 ± 0.89[c] | 512 ± 7[d] | 4.74 ± 0.36[d] |
| STZ + Zn-Insulin | 38.75 ± 3.26[d] | 12.14 ± 0.76[c] | 552 ± 6[c] | 5.98 ± 0.29[c] |
| STZ + Cr-Insulin | 65.00 ± 2.63[b] | 16.71 ± 0.62[b] | 590 ± 7[b] | 7.81 ± 0.35[b] |
| p < | 0.0001 | 0.0001 | 0.0001 | 0.0001 |

[1]Rats in control group was injected with saline. STZ = streptozotocin (STZ, 40 mg/kg i.p.); STZ + Zn-Insulin = STZ + Zn-insulin (0.5 IU); STZ + Cr-Insulin = STZ + Cr-insulin (0.8 IU) daily for 8 weeks.
[2]Different superscripts within columns differ (p < 0.05).

As shown in Table 6, compared to all other treatment groups including ZnIns, CrIns resulted in the highest levels of serum chromium levels, brain chromium levels, brain serotonin levels, and brain tryptophan levels. These data suggest that CrIns is superior to ZnIns to suppress hyperglycemia and treat diabetes.

TABLE 8

Effect of insulin-chelate type on bands (n = 7 per group).

| Group[1] | Response variables[2] | | | | | |
|---|---|---|---|---|---|---|
| | Kidney oct1 | Kidney oct2 | Kidney nfk | Kidney mrp2 | Brain nfk | Brain ins |
| Cntrl. | 100.00 ± 2.81[a] | 100.00 ± 3.00[a] | 100.00 ± 1.84[c] | 100.00 ± 2.58[c] | 100.00 ± 2.80[c] | 100.00 ± 5.41[a] |
| STZ | 36.56 ± 2.84[e] | 35.03 ± 1.71[e] | 156.54 ± 9.31[a] | 175.38 ± 4.33[a] | 221.68 ± 2.80[a] | 40.10 ± 3.03[e] |
| STZ + Zn | 50.02 ± 2.05[d] | 51.38 ± 1.17[d] | 120.31 ± 1.65[b] | 148.73 ± 2.74[b] | 150.59 ± 2.73[b] | 44.08 ± 3.31[e] |
| STZ + Cr | 50.90 ± 1.71[d] | 53.50 ± 1.13[d] | 118.86 ± 1.47[b] | 140.21 ± 2.05[b] | 134.24 ± 4.10[b] | 47.89 ± 4.67[e] |
| STZ + Zn-Ins | 74.79 ± 1.66[c] | 70.41 ± 3.49[c] | 90.41 ± 3.30[c] | 92.79 ± 4.60[c] | 106.06 ± 9.04[c] | 78.68 ± 4.25[b] |
| STZ + Cr-Ins | 86.28 ± 1.72[b] | 81.87 ± 5.46[b] | 85.80 ± 8.87[c] | 89.10 ± 4.29[c] | 89.90 ± 8.58[c] | 88.31 ± 2.71[ab] |
| | 0.0001 | 0.0001 | 0.0001 | 0.0001 | 0.0001 | 0.0001 |

[1]Rats in control group was injected with saline. STZ = streptozotocin (STZ, 40 mg/kg i.p.); STZ + Zn-Insulin = STZ + Zn-insulin (0.5 IU); STZ + Cr-Insulin = STZ + Cr-insulin (0.8 IU) daily for 8 weeks.
[2]Different superscripts within columns differ (p < 0.05).

Figure 7:
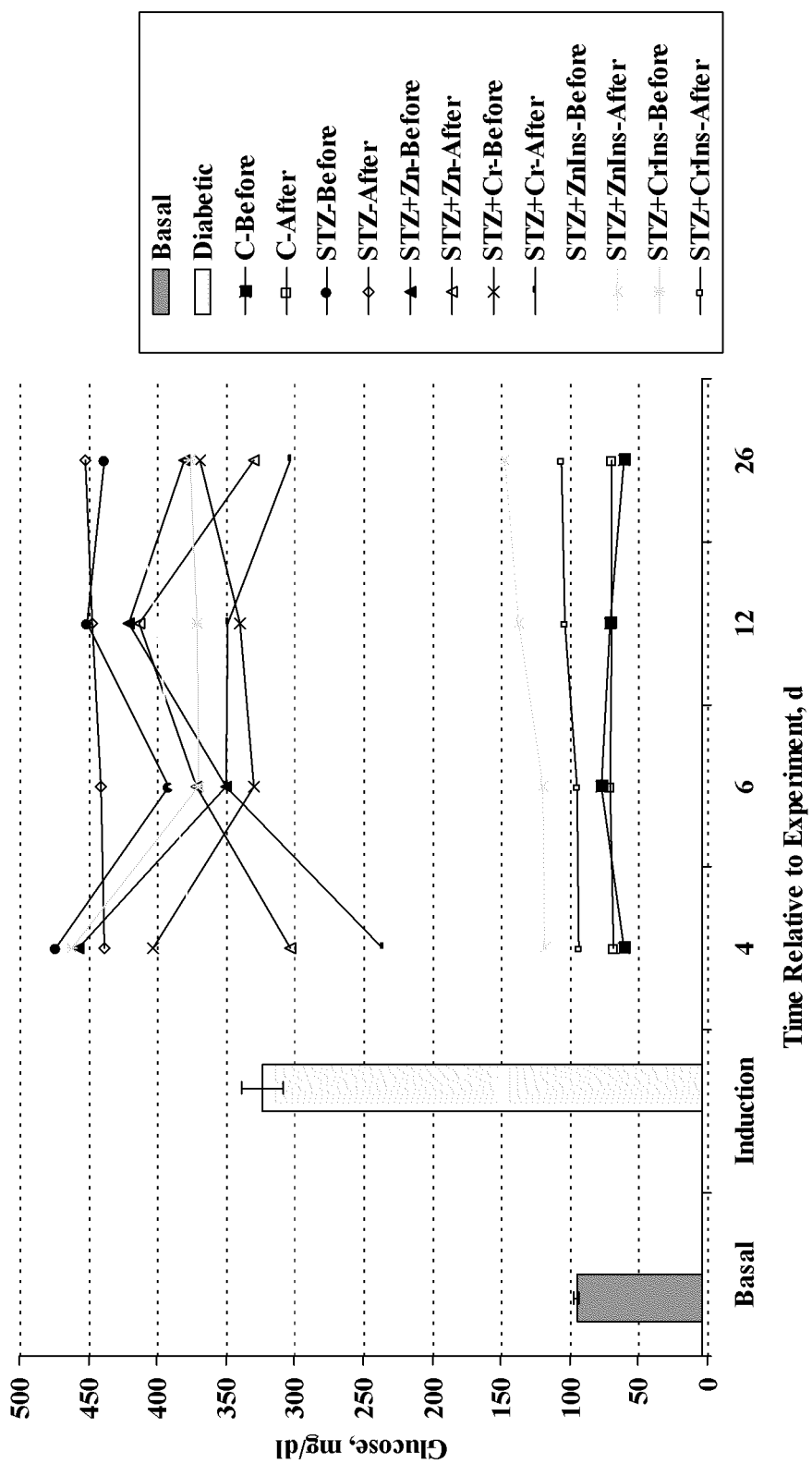
FIG. 7 is a bar and line graph showing the effect of insulin-chelate type on glucose levels of type-1 diabetes induced rats, as described in Example 3. In addition to control (no treatment), five treatment groups were respectively administered the following: streptozotocin (STZ); streptozotocin and zinc oxide (STR+Zn); streptozotocin and chromium histidinate (STZ+CrHis); streptozotocin, zinc oxide, and insulin (STR+ZnIns); and, streptozotocin, chromium histidinate, and insulin (STR+CrIns).

As shown in Table 7 and FIG. 7, administration of the CrIns combination resulted in post-administration serum-glucose levels of approximately 100 mg/dl, which is a desirable euglycemic level. The post-administration serum glucose levels for the ZnIns combination varied from approximately 120-150 mg/dl. These data suggest that CrIns is superior to ZnIns to suppress hyperglycemia and treat diabetes.

Figure 8:
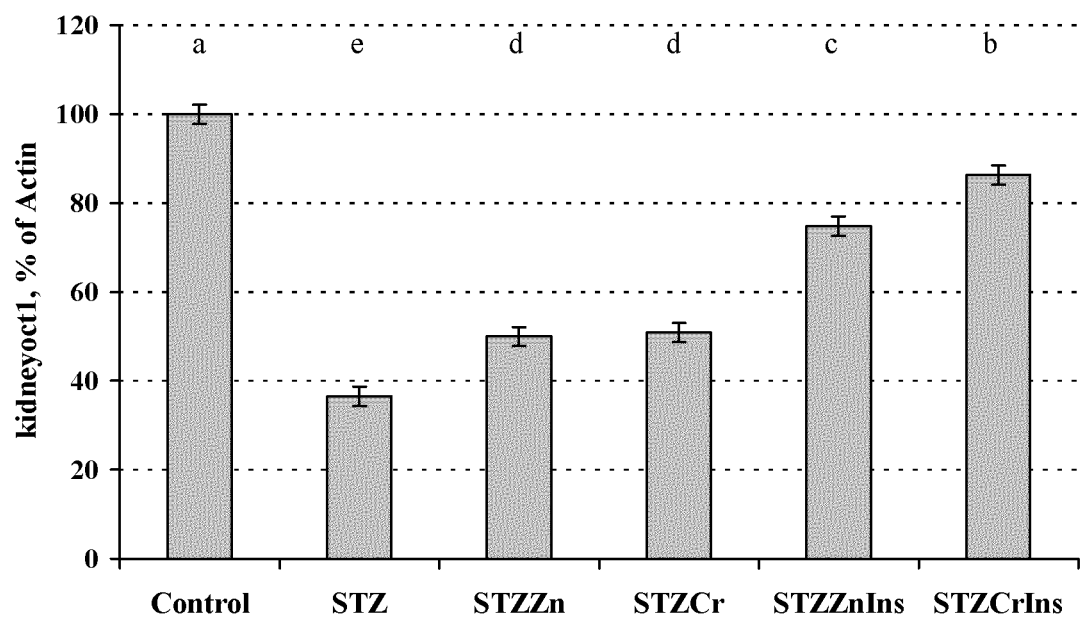
FIG. 8 is a bar graph showing kidney OCT-1 (organic cation transporter 1) levels after treatment for control and treatment groups (STR, STR+Zn, STR+Cr, STR+ZnIns, and STR+CrIns), as described in Example 3.
Figure 9:
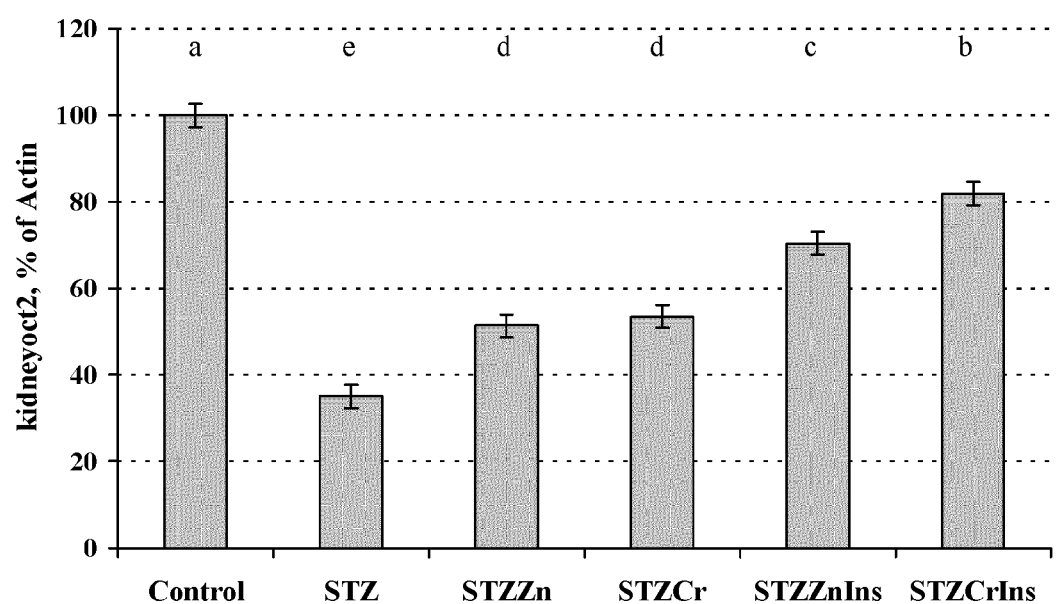
FIG. 9 is a bar graph showing kidney OCT-2 (organic cation transporter 1) levels after treatment for control and treatment groups (STR, STR+Zn, STR+Cr, STR+ZnIns, and STR+CrIns), as described in Example 3.

As shown in Table 7 and FIGS. 8 and 9, the CrIns combination resulted in the highest percentages of kidney OCT-1 and OCT-2 (organic cation transporters) as compared to control levels. OCTs are important for the renal homeostasis of a number of physiologically important endogenous cations, including monoamine neurotransmitters, agmatine, and prostaglandins. OCTs are also necessary for the renal clearance of a broad range of exogenous substrates, including toxins, xenobiotics, and commonly used drugs (e.g., metformin and β-blockers). (Thomas et al (2004) JPET 311:456-466). These data suggest that CrIns may enhance the efficacy of some diabetes drugs, including for example, metformin.

Figure 10:
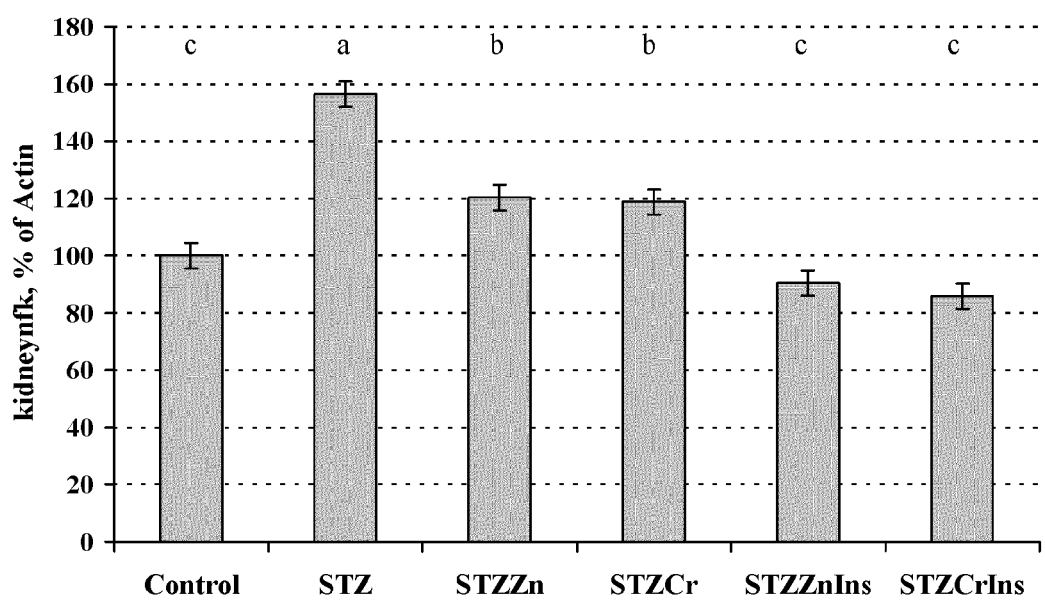
FIG. 10 is a bar graph showing kidney NFK (nuclear factor kappa B) levels after treatment for control and treatment groups (STR, STR+Zn, STR+Cr, STR+ZnIns, and STR+CrIns), as described in Example 3.

As shown in Table 7 and FIG. 10, the CrIns combination resulted in the lowest percentage of kidney NFK (nuclear factor kappa B) as compared to control levels. NFK is a protein transcription factor that is required for maximal transcription of a wide array of pro-inflammatory molecules which are thought to be important in the generation of acute inflammation. (Christman et al. (2000) Brain Pathology 10:153-162). NFK activation induced by long-lasting oxidative stress has been shown to be responsible for neuronal damage and consequent promotion of cell death. (Aragano et al (2002) Endocrinology 143(9):3250-3258).

Figure 11:
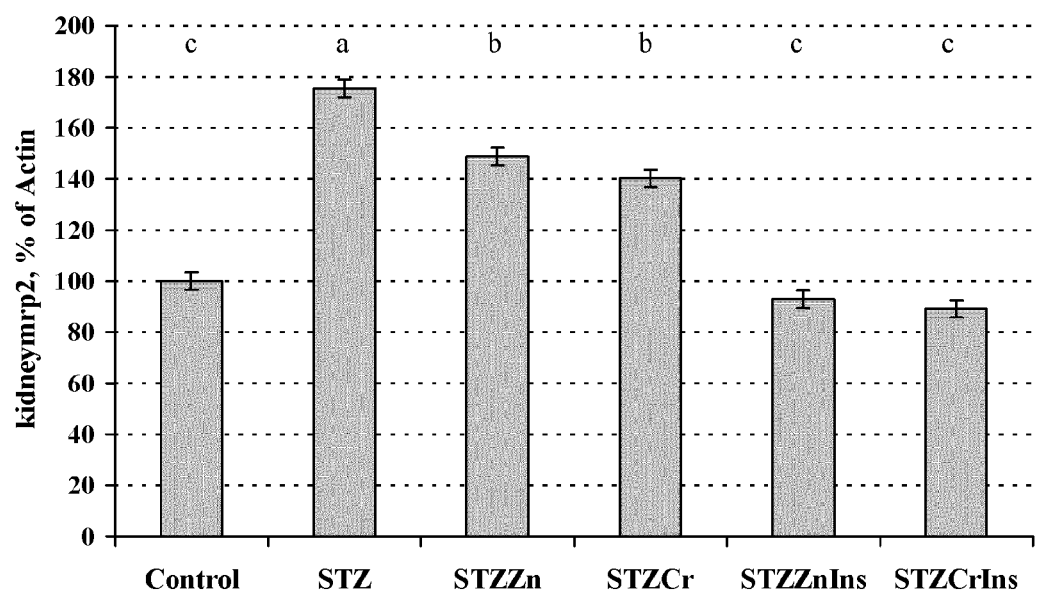
FIG. 11 is a bar graph showing kidney MRP2 (multidrug resistance protein 2) levels after treatment for control and treatment groups (STR, STR+Zn, STR+Cr, STR+ZnIns, and STR+CrIns), as described in Example 3.

As shown in Table 7 and FIG. 11, the CrIns combination resulted in the lowest percentage of kidney MRP2 (multidrug resistance related protein 2) as compared to control levels. MRP2 is an ATP-binding cassette (ABC) transporter that functions in the organic anion transport system. (Sekine et al. (2006) Am. J. Physiol Renal Physiol 290:F251-F261).

Figure 12:
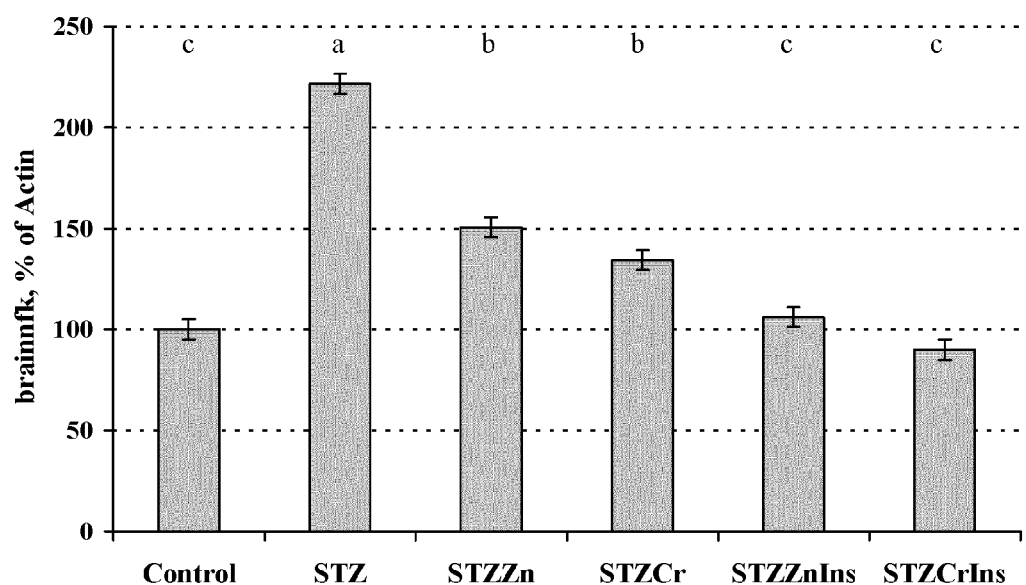
FIG. 12 is a bar graph showing brain NFK levels after treatment for control and treatment groups (STR, STR+Zn, STR+Cr, STR+ZnIns, and STR+CrIns), as described in Example 3.

As shown in Table 7 and FIG. 12, the CrIns combination resulted in the lowest percentage of brain NFK as compared to control levels.

Figure 13:
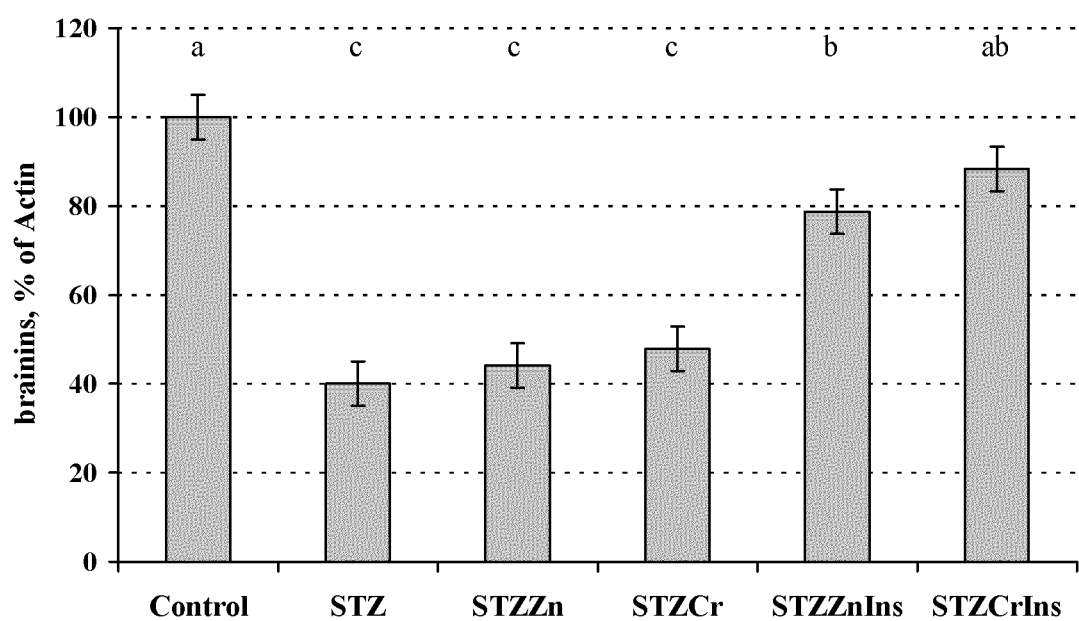
FIG. 13 is a bar graph showing brain insulin levels after treatment for control and treatment groups (STR, STR+Zn, STR+Cr, STR+ZnIns, and STR+CrIns), as described in Example 3.

As shown in Table 7 and FIG. 13, the CrIns combination resulted in the highest percentage of brain insulin levels as compared to control levels. These data suggest that CrIns is superior to ZnIns to suppress hyperglycemia and treat diabetes.

Example 9

A subject is identified as having early stage Alzheimer's disease. The subject presents with one or more symptoms including memory changes that disrupt daily life, challenges in planning or solving problems, difficulty in completing familiar tasks, confusion with time or place, trouble understanding visual images and spatial relationships, new problems with words in speaking or writing, misplacing things and losing the ability to retrace steps, decreased or poor judgment, withdrawal from work or social activity, and changes in mood and personality.

The subject is administered a composition comprising between 50 μg and 5000 μg chromium and between 1 unit and 500 units of insulin. The composition is administered parenterally. The subject's condition, as assessed by one or more symptoms of the disease, does not worsen, or improves, over time.

Example 10

A subject is identified as having Alzheimer's disease by a routine dementia screening test, such as a clock drawing test, a time and change test, a sniff test, or the like, and/or shows symptoms of Alzheimer's as evidenced by a PET scan.

The subject is administered a composition comprising between 50 µg and 5000 µg chromium and between 1 unit and 500 units of insulin. The composition is administered parenterally. The subject's condition, as assessed by one or more symptoms of the disease, does not worsen or improves over a period of five days.

Example 11

A subject is identified as having Parkinson's disease by conventional methods. The subject presents with one or more symptoms including tremors, stiffness (or rigidity) of muscles, slowness of movement (bradykinesia) and loss of balance (postural dysfunction).

The subject is administered a composition comprising between 50 µg and 5000 µg chromium and between 1 unit and 500 units of insulin. The composition is administered parenterally. The subject's condition, as assessed by one or more symptoms of the disease, does not worsen, or improves, over time.

Example 12

A subject is identified as having mild cognitive impairment. The subject presents one or more symptoms including memory complaints corroborated by an informant, objective memory impairment for age and education, normal general cognitive function, intact activities of daily living, and the subject does not meet criteria for dementia The subject is administered a composition comprising between 50 µg and 5000 µg chromium and between 1 unit and 500 units of insulin. The composition is administered parenterally. The subject's condition, as assessed by one or more symptoms of the disease, does not worsen, or improves, over time.

Example 13

A subject presents with symptoms of ADHD, including inattention (e.g. failure to give close attention, difficulties in sustaining attention, difficulties in organizing tasks and activities and easily distracted by extraneous stimuli), hyperactivity (e.g. difficulties in remaining seated, excessive motor activity in inappropriate situations, the patient acts as if "driven by a motor"), and impulsivity (e.g. difficulties in awaiting turn, answer questions before they have been completed and often interrupts or intrudes ongoing conversation).

The subject is administered a composition comprising between 50 µg and 5000 µg chromium and between 1 unit and 500 units of insulin. The composition is administered parenterally. The subject's condition, as assessed by one or more symptoms of the disease, does not worsen, or improves, over time.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A composition consisting essentially of a chromium-insulin complex that is insoluble in deionized water at room temperature, wherein the chromium-insulin complex comprises between 4 and 6 chromium ions and six molecules of insulin, and wherein the chromium-insulin complex is formulated for administration to a subject.

2. The composition of claim 1, wherein the composition is formulated for injection into a subject.

3. The composition of claim 1, wherein the amount of chromium-insulin complex is effective to reduce weight gain in a subject having type 2 diabetes.

4. The composition of claim 1, wherein the amount of chromium-insulin complex is effective to reduce weight loss in a subject having type 1 diabetes.

5. The composition of claim 1, wherein the chromium-insulin complex has a molecular weight between 5 kDa and 50 kDa.

6. The composition of claim 1, wherein the chromium-insulin complex has a molecular weight of about 33 kDa.

7. The composition of claim 1, wherein the composition comprises between 5 micrograms and 2,000 micrograms of chromium.

8. The composition of claim 1, wherein composition comprises between 1 unit and 500 units of insulin.

9. The composition of claim 1, wherein the chromium-insulin complex is suspended in a solution.

10. The composition of claim 1, further comprising a nutritionally acceptable carrier.

11. The composition of claim 1, wherein the chromium-insulin complex is in an aqueous solution.

12. A composition consisting essentially of a therapeutically effective amount of a purified chromium-insulin complex that is insoluble in deionized water at room temperature, wherein the chromium-insulin complex comprises between 4 and 6 chromium ions and six molecules of insulin, and wherein the chromium-insulin is formulated for administration to a subject.

* * * * *